US007271238B2

(12) United States Patent
Gaeta et al.

(10) Patent No.: US 7,271,238 B2
(45) Date of Patent: *Sep. 18, 2007

(54) AMYLIN AGONIST PEPTIDES AND USES THEREFOR

(75) Inventors: Laura S. L. Gaeta, La Jolla, CA (US); Howard Jones, Poway, CA (US); Elisabeth Albrecht, San Diego, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 388 days.

This patent is subject to a terminal disclaimer.

(21) Appl. No.: 10/649,138

(22) Filed: Aug. 26, 2003

(65) Prior Publication Data

US 2004/0038900 A1 Feb. 26, 2004

Related U.S. Application Data

(60) Continuation of application No. 09/454,533, filed on Dec. 6, 1999, now Pat. No. 6,610,824, which is a continuation of application No. 08/892,549, filed on Jul. 14, 1997, now Pat. No. 5,998,367, which is a division of application No. 08/447,849, filed on May 23, 1995, now Pat. No. 5,686,411, which is a continuation of application No. 07/794,266, filed on Nov. 19, 1991, now abandoned, which is a continuation-in-part of application No. 07/667,040, filed on Mar. 8, 1991, now abandoned.

(51) Int. Cl.
*A61K 38/16* (2006.01)

(52) U.S. Cl. .................. 530/324; 530/300; 514/2; 514/12

(58) Field of Classification Search ................ None
See application file for complete search history.

(56) References Cited

U.S. PATENT DOCUMENTS

| 4,743,677 | A | | 5/1988 | Noda et al. | |
|---|---|---|---|---|---|
| 4,988,512 | A | * | 1/1991 | Azria | ................... 424/422 |
| 4,992,530 | A | | 2/1991 | Morita et al. | |
| 5,112,945 | A | | 5/1992 | Westermark et al. | |
| 5,116,948 | A | | 5/1992 | Westermark et al. | |
| 5,124,314 | A | | 6/1992 | Cooper | |
| 5,175,145 | A | | 12/1992 | Cooper | |
| 5,234,906 | A | | 8/1993 | Young et al. | |
| 5,266,561 | A | | 11/1993 | Cooper et al. | |
| 5,281,581 | A | | 1/1994 | Cooper et al. | |
| 5,298,605 | A | | 3/1994 | Westermark et al. | |
| 5,321,008 | A | | 6/1994 | Beaumont et al. | |
| 5,367,052 | A | | 11/1994 | Cooper et al. | |
| 5,405,831 | A | | 4/1995 | MacIntyre et al. | |
| 5,424,221 | A | | 6/1995 | Westermark et al. | |
| 5,424,394 | A | | 6/1995 | Lehman De Gaeta et al. | |
| 5,508,260 | A | | 4/1996 | Beaumont et al. | |
| 5,527,771 | A | | 6/1996 | Beaumont et al. | |
| 5,580,953 | A | * | 12/1996 | Albrecht et al. | ............ 530/303 |
| 5,641,744 | A | | 6/1997 | Cooper et al. | |
| 5,656,590 | A | | 8/1997 | Rink et al. | |
| 5,686,411 | A | * | 11/1997 | Gaeta et al. | ................... 514/12 |
| 5,814,600 | A | * | 9/1998 | Rink et al. | ...................... 514/4 |
| 5,998,367 | A | * | 12/1999 | Gaeta et al. | ................... 514/12 |
| 6,114,304 | A | * | 9/2000 | Kolterman et al. | ........... 514/12 |
| 6,417,164 | B1 | * | 7/2002 | Kolterman et al. | ........... 514/12 |
| 6,610,824 | B2 | * | 8/2003 | Gaeta et al. | ................ 530/324 |
| 2004/0097415 | A1 | * | 5/2004 | Kolterman et al. | ........... 514/12 |

FOREIGN PATENT DOCUMENTS

| EP | 0 309 100 | 3/1989 |
|---|---|---|
| EP | 0 408 294 | 7/1990 |
| WO | WO 89/06135 | 7/1989 |
| WO | WO 90/06936 | 6/1990 |
| WO | WO 92/11862 | 7/1992 |
| WO | WO 92/11863 | 7/1992 |
| WO | WO 92/15317 | 9/1992 |
| WO | WO 93/10146 | 5/1993 |

OTHER PUBLICATIONS

Young, "Daily amylin replacement reverses hepatic glycogen depletion in insulin-treated streptozotocin diabetic rats" FEBS 1991, 287(1-2), 203-205.*
Berge et al. "Pharmaceutical Salts" J. Pharm. Sci. 1997, 66(1), 1-16.*
Sanke et al. "An Islet Mayloid Peptide is derived from an 89-amino acid precursor by proteolytic processing" J. Biol. Chem. 1988, 263(33), 17243-17246.*
Bell, "Molecular Defects in Diabetes-Mellitus", *Diabetes*, 40:413-422 (1991).
Betsholtz et al., "Islet Amyloid Polypeptide (IAPP): cDNA Cloning and Identification of an Amyloidogenic Region Associated with the Species-Specific Occurrence of Age-Related Diabetes Mellitus", *Experimental Cell Research*, 183:484-493 (1989).
Betsholtz et al., "Sequence divergence in a specific region of islet amyloid polypeptide (IAPP) explains differences in islet amyloid formation between species", *FEBS Letters*, 251:261-264 (1989).
Clark et al., "Islet Amyloid Formed From Diabetes-Associated Peptide May be Pathogenic in Type-2 Diabetes", *The Lancet*, 2(8553):231-234 (1987).
Cooper et al., "Aylin and the amylin gene: strructure, function, and relationship to islet amyloid and to diabetes mellitus", *Biochem. Biophys, Acta.*, 1014:247-258 (1989).

(Continued)

Primary Examiner—Jon Epperson
(74) Attorney, Agent, or Firm—Amylin IP Group

(57) ABSTRACT

Agonist analogues of amylin and related pharmaceutical compositions, and methods of treatment of diabetes and other insulin-requiring states, as well as methods of treatment of hypoglycemia, are provided.

19 Claims, 3 Drawing Sheets

OTHER PUBLICATIONS

Cooper et al., "The Amylin Superfamily: A Novel Grouping of Biologically Active Polypeptides Related to the Insulin A-Chain", *Prog. Growth Factor Research*, 1:99-105 (1989).

Cooper et al., "Purification and characterization of a peptide from amyloid-rich pancreases of type 2 diabetic patients", *Proc. Natl. Acad. Sci.*, 84:8628-8632 (1987).

Cooper et al., "Amylin Found In Amyloid Deposits In Human Type 2 Diabetes Mellitus May Be A Hormone That Regulates Glycogen Metabolism In Skeletal Muscle", *Proc. Natl. Acad. Sci.*, 85:7763-7766 (1988).

Cooper et al., "Amylin and Non-Insulin-Dependent (Type 2) Diabetes Mellitis", *Diabetes 1988*, ed. Larkins, R., Zimmet, P. & Chisholm, D. (Elsevier, Amsterdam), pp. 493-496 (1989).

Dayoff et al., "A Model off evolutionary Change in Proteins", *Atlas of Protein Sequences & Structure*, vol. 5, pp. 89-99 (1972).

Deems et al., "Amylin of CGRP (8-37) Fragments Reverse Amylin-induced Inhibition of $^{14}$C-Glycogen Accumulation", *Biochem. Biophys. Res. Commun.*, 181(1):116-120 (1991).

Doherty, "Endogenous Vasoactive Peptides", *Annual Reports in Medicinal Chemistry*, 26:83-92 (1991).

Fujii et al., "Synthesis of Second Human Calcitonin Gene-Related Peptide (β-hCGRP) by Application of a New Disulfide-Bonding Reaction with Thallium(III) Trifuoroacetate", *Chem. Pharm. Bull.*, 35(12):4769-4776 (1987).

Fujii et al., "Syntheses of Cystine-Peptides by Oxidation of S-Protected Cysteine-Peptides with Thallium(III) Trifluoroacetate", *Chem. Pharm. Bull.*, 35(6):2339-2347 (1987).

Glenner et al., "Amyloid Fibrils Formed from a Segment of the Pancreatic Islet Amyloid Protein", *Biochem. Biophys. Res. Commun.*, 155(2):608-612 (1988).

Goodman and Gilman's "The Pharmacological Basis of Therapeutics", Chapter 38 Pergamon Press, Eighth Edition (1990).

Gustavsson et al., "Normal Transthyretin and Synthetic Transthyretin-Fragments form Amyloid-Like Fibrils in Vitro", *Biochem. Biophys. Res. Commun.*, 175(3):1159-1164 (1991).

Hilbich et al., "Aggregation and Secondary Structure of Synthetic Amyloid .beta.A4 Peptides of Alzheimer's Disease", *J. Mol. Biol.*, 218:149-163 (1991).

Hiskey et al., "Sulfhydryl Group Protection in Peptide Synthesis", *The Peptides*, vol. 3, Chapter 3, pp. 137-167 (1981).

Hubbard et al., "Soluiton strucutres of Calcitonin-gene-related-peptide analogues of calcitonin-gene-related-peptide and amylin", *Biochem. J.*, 275:785-788 (1991).

Johnson et al., "Islet Amyloid Polypeptide: Mechanisms of Amyloidogenesis in the Pancreatic Islets and Potential Roles in Diabetes Mellitus", *Laboratory Investigation*, 66(5):522-535 (1992).

Johnson et al., "Factors Affecting Diabetogenesis and Amyloidogenesis are Provided by Studies of IAPP in the Dog and Cat", In Natvig, J.B. et al., Editors, Amyloid and Amyloidogenesis, 1990. Norwall, Mass, Kluwer Academic Publishers, pp. 445-448 (1991).

Johnson et al., "Islet Amyoid, Islet-Amyloid Polypeptide, and Diabetes Mellitus", *New England Journal of Medicine*, 321(8):513-518 (1989).

Johnson et al., "Newly Identified Pancreatic Protein Islet Amyloid Polypeptide", *Diabetes*, 40:310-314 (1991).

Johnson et al., "Amyloid in the Pancreatic Islets of the Cougar (Felis Concolor) is derived from Islet Amyloid Polypeptide (IAPP)", *Comp. Biochem. Physiol.*, 98B(1):115-119 (1991).

Jordan et al., "Canine IAPP cDNA Sequence Provides Important Clues Regarding Diabetogenesis and Amyloidogenesis in Type 2 Diabetes", *Biochemical and Biophysical Research Communications*, 169(2):502-508 (1990).

Leffert et al., "Rat amylin: Cloning and tissue-specific expression in pancreatic islets", *Proc. Natl. Acad. Sci. (PNAS)*, 86:3127-3130 (1989).

Leighton et al., "Pancreatic amylin and calcitonin gene-related peptide cause resitance to unsulin in skeletal muscle in vitro", *Nature*, 335(6191):632-635 (1988).

Leighton et al., "Amlin inhibits glucose utilization in the soleus muscle of the rat in vitro", *Diabetologia*, 31:513 A [Abstract 288] (1988).

Nishi et al., "Conservation of the sequence of islet amyloid polypeptide in five mammals is consistent with its putative role as an islet hormone", *Proc. Natl. Acad. Sci.*, 86:5738-5742 (1989).

O'Brien et al., "Islet Amyloid Polypeptide and Insulin Secretion from Isolated Perfused Pancreas of Fed, Fasted, Glucose-Treated, and Dexamethasone-Treated Rats", *Diabetes*, 40:1701-1706 (1991).

Ohagi et al., "Sequence of islet amyloid polypeptide precursors of an old world monkey, the pig-tailed macaque (*Macaca nemestrina*), and the dog (*Canis familaris*)", *Diabetologia*, 34:555-558 (1991).

Pettersson et al., "Calcitonin Gene-related Peptide: Occurrence in Pancreatic Islets in the Mouse and the Rat and Inhibition of Insulin Secretion in the Mouse", *Endocrinology*, 119(2):865-869 (1986).

Porte et al., "62 -Cells in Type II Diabetes Mellitus", *Diabetes*, 40:166-180 (1991).

Poyner, "Pharmacology of receptors for calcitonin gene-related pepide and amylin", *TIPS*, 16(12):424-428 (1995).

Roberts et al., "Molecular and functional characterization of amylin, a peptide associated with type 2 diabetes mellitus", *Proc. Natl. Acad. Sci. (PNAS)*, 86:9662-9666 (1989).

Saldanha et al., "Molecular model-building of amylin and α-calcitonin gene-related polypeptide hormones using a combination of knowledge sources", *Protein Engineering*, 4(5):539-544 (1991).

Stridesberg et al., "Islet Amyloid Polypeptide (IAPP)", *Acta Oncologica*, 30(4):451-456 (1991).

Westermark et al., "A Novel Peptide in the Calcitonin Gene Related Peptide Family as an Amyloid Fibril Protein in the Endocrine Pancreas", *Biological and Biophysical Research Communications*, 140(3):827-831 (1986).

Westermark et al., "Islet Amyloid in Type 2 Human Diabetes Mellitus and Adult Diabetic Cats Contains a Novel Putative Polypeptide Hormone", *Am. J. Pathology.*, 127(3):414-417 (1987).

Westermark et al., "Islet Amyloid Polypeptide: Pinpointing Amino Acid Residues Linked to Amyloid Fibril Formation", *Proc. Natl. Acad. Sci.*, 87:5036-5040 (1990).

Westermark et al., "Islet amyloid polypeptide (IAPP) and pro-IAPP immunoreactivity in human islets of Langerhans", *Diabetes Research and Clinical Practice*, 7:219-226 (1989).

Westermark, "Islet amyloid polypeptide in humans and cats", in *Frontiers in diabetes research, Lessons from animal diabetes III*, Shafrir, E., Eds., X.2:498-501, Smith-Gordon (1990).

Bell, G.I., "Molecular Defects in Diabetes Mellitus," *Diabetes* 40:413-422 (1991).

Betsholtz, C. et al., "Islet Amyoid Polypeptide (IAPP): cDNA Cloning and Identification of an Amyloidogeneic Region Associated with the Species-Specific Occurence of Age-Related DIabetes Mellitus," *Experimental Cell Research* 183: 484-493 (1989).

Betsholtz et al., "Sequence divergence in a specific region of islet amyloid polypeptide (IAPP) explains differences in islet amyloid formation between species," *FEBS Letters* 251:261-264 (1989).

Clark et al., "Islet Amyloid Formed From Diabetes-Associated Peptide May be Pathogenic in Type-2 Diabetes," *The Lancet* 2(8553): 231-234 (1987).

Cooper et al., "Amylin Found in Amyloid Deposits in Human Type 2 Diabetes Mellitus May be a Hormone that Regulates Glycogen Metabolism in Skeletal Muscle," *Proc Natl Acad Sci* 85:7763-7766 (1988).

Copper et al., "Amylin and the amylin gene: structure, function and relationship to islet amyloid and to diabetes mellitus," *Biochem. Biophys. Acta.*, 1014:247-258, 1989.

Cooper et al., "The Amylin Superfamily: A Novel Grouping of Biological Active Polypeptides Related to the Insulin A-Chain," *Prog. Growth Factor Research*, 1:99-105, 1989.

Cooper et al., "Purification and characterization of a peptide from amyloid-rich pancreases of type 2 diabetic patients," *Proc Natl Acad Sci* 84: 8628-8632 (1987).

Cooper et al., "Amylin and Non-Insulin-Dependent (Type 2) Diabetes Mellitus," in *Diabetes* 1988 ed. Larkins, R., Zimmet, P. & Chisholm, D. (Elsevier, Amsterdam) pp. 493-496 (1989).

Dayoff et al., "A Model of evoluitonary Change in Proteins," *Atlas of Protein Sequences & Structure*, vol. 5, pp. 89-99 (1972).

Deems et al., "Amylin of CGRP (8-37) Fragments Reverse Amylin-induced Inhibition of $^{14}$C-Glycogen Accumulation," *Biochem. Biophys. Res. Commun.*, 181(1):116-120, 1991.

Doherty, "Endogenous Vasoactive Peptides," *Annual Reports in Medicianal Chemistry*, 26: 83-92 (1991).

Fujii, N. et al., "Synthesis of Second Human Calcitonin Gene-Related Peptide (β-hCGRP) by Application of a New Disulfide-Bonding Reaction with Thallium(III) Trifuoroacetate," *Chem. Pharm. Bull*, 35(12): 4769-4776 (1987).

Fujii, N. et al., "Synthesis of Cystine-Peptides by Oxidation of S-Protected Cysteine-Peptides with Thallium(III) Trifuoroacetate," *Chem. Pharm. Bull*. 35(6): 2339-2347 (1987).

Glenner et al., "Amyloid Fibrils Formed from a Segment of the Pancreatic Islet Amyloid Proteins," *Biochem Biophys Res Commmun* 155(2): 608-614 (1988).

Goodman and Gilman's "The Pharmacological Basis of Therapeutics," Chapter 38 Pergamon Press, Eighth Edition, Eighth Edition (1990).

Gustavsson et al., "Normal Transthyretin and Synthetic Transthyretin-Fragments form Amyloid-Like Fibrils in Vitro," *Biochem Biophys Res Commun* 175(3):1159-1164 (1991).

Hilbich, et al., "Aggregation and Secondary Structure of Synthetic Amyloid βA4 Peptides of Alzheimer's Disease," *J Mol Biol* 218: 149-163 (1991).

Hiskey, R.G.. et al., "Sulfydryl Group Protection in Peptide Synthesis," in *The Peptides, Analysis, Synthesis, Biology*, Gross, E., Ed., Chapter 3, pp. 137-167 (1981).

Hubbard , J.A.M. et al., "Solution structures of calcitonin-gene-related-peptide analogues of calcitonin-gene-related-peptide and amylin," *Biochem. J*. 275: 785-788 (1991).

Johnson, K.H. et al., "Islet Amyloid Polypeptide: Mechanisms of Amyloidogenesis in the Pancreatic Islets and Potential Roles in Diabetes Mellitus," *Laboratory Investigation* 66(5): 522-535 (1992).

Johnson, K.H. et al., "Factors Affecting Diabetogenesis and Amyloidogenesis are Provided by Studies of IAPP in the Dog and Cat," In Amyloid and Amyloidogenesis Natvig, J.B. et al., Editors, , 1990. Norwall, Mass, Kluewer Academic Publishers, pp. 445-448 (1991).

Johnson, K.H. et al., "Islet Amyoid, Islet-Amyloid Polypeptide, and Diabetes Mellitus," *New Englang Journal of Medicine* 321(8): 513-518 (1989).

Johnson, K.H., et al., "Newly Identified Pancreatic Protein Islet Amyloid Polypeptide," *Diabetes* 40: 310-314 (1991).

Johnson, K.H., et al., "Amyloid in the Pancreatic Islets of the Couger (*Felis Concolor*) is derived from Islet Amyloid Polypeptide (IAPP)" *Comp Biochem Physiol* 98B(1): 115-119 (1991).

Jordan, K. et al., "Canine IAPP cDNA Sequence Provides Important Clues Regarding Diabetogenesis and Amyloidogenesis in Type 2 Diabetes," *Biochemical and Biophysical Research Communications* 169(2): 502-508 (1990).

Leffert et al, "Rat amylin: Cloning and tissue-specific expression in pancreatic islets," *Proc Natl Acad Sci (PNAS)*, 86:3127-3130 (1989).

Leighton et al., "Pancreatic amylin and calcitonin gene-related peptide cause resistance to insulin in skeletal muscle in vitro," *Nature*, 335:632-635 (1988).

Leighton, B., Cooper, G.J.S., "Amylin inhibits glucose utilization in the soleus muscle of the rat in vitro," *Diabetologia*, 31: 513 A [abstract 288] (1988).

Nishi et al., "Conservation of the sequence of islet amyloid polypeptide in five mammalsis consistent with its putative role as an islet hormone," *Proc. Natl. Acad. Sci*. 86(15):5738-5742 (1989).

O'Brien, T.D., et al., "Islet Amyloid Polypeptide and Insulin Secretion from Isolated Perfused Pancreas of Fed, Fasted, Glucose-Treated, and Dexamethasone-Treated Rats", *Diabetes*, 40:1701-1706 (1991).

Ohagi, S., et al., "Sequences of islet amyloid polypeptide precursors of an old world monkey, the pig-tailed macaque (*Macaca nemestrina*), and the dog (*Canis familaris*)", *Diabetologia*, 34:555-558 (1991).

Pettersson, M. et al., "Calcitonin Gene-related Peptide: Occurrence in Pancreatic Islets in the mouse and the rat and Inhibition of insulin secretion in the mouse", *Endocrinology*, 119(2):865-869 (1986).

Porte, D., et al., "62 -Cells in Type II Diabetes Mellitus", *Diabetes*, 40: 166-180 (1991).

Poyner, "Pharmacology of receptors for calcitonin gene-related pepide and amylin," *Trends in Pharm. Sci*. 16(12):424-428 (1995).

Roberts et al., "Molecular and functional characterization of Amylin, a peptide associated with type 2 diabetes mellitus", *Proc. Natl. Acad. Sci*. (*PNAS*), 86:9662-9666 (1989).

Saldanha, J. et al., "Molecular model-building of amylin and α-calcitonin gene-related polypeptide hormones using a combination of knowledge sources", *Protein Engineering*, 4(5):539-544 (1991).

Steiner, et al. "Is Islet Amyloid Polypeptide A Significant Factor in Pathogenesis of Pathophysiology of Diabetes?" *Diabetes* 40:305-309 (1991).

Stridsberg and Wilander, "Islet Amyloid Polypeptide: Pinpointing Amin Acid Residues Linked to Amyloid Fibril Formation", *Proc Natl Acad Sci* (*USA*) 87:5036-5040 (1990).

Stridsberg, M., et al., "Islet Amyloid Polypeptide (IAPP)" *Acta Oncologica* 30(4): 451-456 (1991).

Westermark et al, "A novel peptide in the calcitonin gene related peptide family as an amyloid fibril protein in the endocrine pancreas," *Biochemical and Biophysical Research Communications*, 140(3):827-831 (1986).

Westermark et al., "Islet Amyloid in type 2 Human Diabetes Mellitus and Adult Diabetic Cats Contains a Novel Putative Polypeptide Hormone," *Am J Pathology*, 127(3):7414-417 (1987).

Westermark et al., "Islet Amyloid Polypeptide: Pinpointing Amino Acid Residues Linked to Amyloid Fibril Formation," *Proc. Natl. Acad. Sci*. 87:5036-5040 (1990).

Westermark, P., et al., "Islet amyloid polypeptide (IAPP) and pro-IAPP immunoreactivity in human islets of Langerhans," *Diabetes Research and Clinical Practice* 7: 219-226 (1989).

Westermark, P., "Islet amyloid polypeptide in humans and cats", in *Frontiers in diabetes research, Lessons from animal diabtes III*, Shafrir, E., Eds. X. 2: 498-501, Smith-Gordon (1990).

\* cited by examiner

FIGURE 1

¹Lys-Cys-Asn-Thr-⁵Ala-Thr-Cys-Ala-Thr-¹⁰Gln-Arg-Leu-Ala-Asn-¹⁵Phe-Leu-Val-His-Ser-²⁰Ser-Asn-Asn-Phe-Gly-²⁵Ala-Ile-Leu-Ser-Ser-³⁰Thr-Asn-Val-Gly-Ser-³⁵Asn-Thr-Tyr-NH₂

FIGURE 2

Amylin

| | |
|---|---|
| human | KCNTATCATQRLANFLVHSSNNFGAILSSTNVGSNTY-NH$_2$ |
| cat | ---------------IR----L-----P--------- |
| dog | ---------------RT----L-----P--------- |
| rat | ---------------R-----L-PV-PP--------- |
| mouse | ---------------R-----L-PV-PP--------- |
| hamster | ------------------N--L-PV--P--------- |
| guinea pig | -----------T----R--H-L--A-LP-D------ |

FIGURE 3

$^1$A$_1$-X-Asn-Thr-$^5$Ala-Thr-Y-Ala-Thr-$^{10}$Gln-Arg-Leu-B$_1$-Asn-$^{15}$Phe-Leu-C$_1$-D$_1$-E$_1$-$^{20}$F$_1$-G$_1$-Asn-H$_1$-Gly-$^{25}$I$_1$-J$_1$-Leu-K$_1$-L$_1$-$^{30}$Thr-M$_1$-Val-Gly-Ser-$^{35}$Asn-Thr-Tyr-Z

AMYLIN AGONIST PEPTIDES AND USES THEREFOR

BACKGROUND

This application is a continuation of application Ser. No. 09/454,533, filed Dec. 6, 1999, now U.S. Pat. No. 6,610,824, which is a continuation of application Ser. No. 08/892,549, filed Jul. 14, 1997, now U.S. Pat. No. 5,998,367, which is a divisional of application Ser. No. 08/447,849, filed May 23, 1995, now U.S. Pat. No. 5,686,411, which is a continuation of application Ser. No. 07/794,266, filed Nov. 19, 1991, now abandoned, which is a continuation-in-part of application Ser. No. 07/667,040, filed Mar. 8, 1991 now abandoned, which prior applications are hereby incorporated by reference in their totalities (including drawings).

FIELD OF THE INVENTION

The field of the invention is medicine, particularly the treatment and prevention of hypoglycemic conditions and other conditions in which enhanced amylin action is of benefit, including insulin-requiring states such as diabetes mellitus. More specifically, the invention relates to the preparation and use of agonist analogues of the peptide hormone amylin.

DESCRIPTION OF RELATED ART AND INTRODUCTION TO THE INVENTION

Diabetes mellitus is a serious metabolic disease that is defined by the presence of chronically elevated levels of blood glucose (hyperglycemia). This state of hyperglycemia is the result of a relative or absolute lack of activity of the peptide hormone, insulin. Insulin is produced and secreted by the β cells of the pancreas. Insulin is reported to promote glucose utilization, protein synthesis, and the formation and storage of neutral lipids. Glucose, the principal source of carbohydrate energy, is stored in the body as glycogen, a form of polymerized glucose, which may be converted back into glucose to meet metabolism requirements. Under normal conditions, insulin is secreted at both a basal rate and at enhanced rates following glucose stimulation, all to maintain metabolic homeostasis by the conversion of glucose into glycogen.

The term diabetes mellitus encompasses several different hyperglycemic states. These states include Type 1 (insulin-dependent diabetes mellitus or IDDM) and Type 2 (non-insulin-dependent diabetes mellitus or NIDDM) diabetes. The hyperglycemia present in individuals with Type I diabetes is associated with deficient, reduced, or nonexistent levels of insulin which are insufficient to maintain blood glucose levels within the physiological range. Treatment of Type 1 diabetes involves administration of replacement doses of insulin, generally by the parenteral route. The hyperglycemia present in individuals with Type II diabetes is initially associated with normal or elevated levels of insulin; however, these individuals are unable to maintain metabolic homeostasis due to a state of insulin resistance in peripheral tissues and liver and, as the disease advances, due to a progressive deterioration of the pancreatic β cells which are responsible for the secretion of insulin. Thus, initial therapy of Type 2 diabetes may be based on diet and lifestyle changes augmented by therapy with oral hypoglycemic agents such as sulfonylureas. Insulin therapy is often required, however, especially in the latter stages of the disease, in attempting to produce some control of hyperglycemia and minimize complications of the disease. Thus, many Type 2 diabetics ultimately require insulin in order to survive.

Amyloid is the name given to extracellular deposits of β sheet protein filaments. Deposits of amyloid material have been reported to be found in pancreas of patients with Type 2 diabetes mellitus. Other studies have indicated that the degree of amyloid depositions increases with the degree of hyperglycemia in humans and the severity of Type 2 diabetes. Chemical analysis of pancreatic amyloid led to the surprising and unexpected discovery of the peptide hormone, amylin. Clark, A., et al., Lancet ii: 231-234 (1987). This peptide was discovered to be comprised of 37 amino acids, none of which are acidic residues, to have a disulfide linkage between the cysteine residues at positions 2 and 7, and to be C-terminally amidated. Amylin is the major protein constituent of the amyloid which is reported to be found in the pancreatic Islets of Langerhans in patients with type 2 diabetes mellitus.

It has been reported that the presence of both the intramolecular cystine bridge and the carboxy terminal amide group in the peptide structure of the synthetic molecule yield the greatest biological activity to inhibit glycogen synthesis in skeletal muscle. E.g., Cooper, G. J. S., et al., *Proc. Natl. Acad. Sci.* (USA) 84:8628-8632 (1987); Cooper G. J. S., et al., in *Diabetes* 1988, ed. Larkins, R., Zimmet, P. & Chisholm, D. (Elsevier, Amsterdam), pp. 493-496 (1989). The amino acid sequence of amylin (see FIG. 1) has 46% homology with human calcitonin gene related peptide 2 (CGRP-2).

One report states that a limited segment of the amylin molecule, residues 20-29, is a potential contributor toward amyloid fibril formation in the islets of Langerhans in Type 2 diabetes mellitus. Glenner et al., *Biochem. Biophys. Res Commun.* 155:608-614 (1988). It has also been reported that amino acid sequence differences between amylins from certain mammalian species occur in this region, and further investigation has focused on identifying residues linked to amyloid formation. Westermark et al., *Proc. Natl. Acad. Sci.* (USA) 87: 5036-5040 (1990). The study of Westermark et al. reported attempts to synthesize various 20-29 amino acid segments of amylin sequences from different species followed by a comparison of their ability to form amyloid fibrils. It was proposed that the residues 25-29 of human amylin were the most strongly amyloidogenic and that the proline-for-serine substitution in position 28, as in several rodent species, significantly inhibited fibril formation in the studied decapeptides.

Amylin is a complex peptide, and the synthesis of bioactive preparations of amylin is laborious. Amylin has also been found to have limited solubility and limited stability in solution. We have found that rat amylin has a higher solubility and stability in solution than human amylin. This may be due in some measure, although this is not known, to the different aggregation properties of the amylins from different species. Only the human, non-human primate, and cat species of amylin have been reported to aggregate to form islet amyloid in vivo. The sequences of amylin now reported to have been isolated from a number of species are set forth in FIG. 2.

In Type I diabetes, amylin levels are severely reduced or are nonexistent when compared to normal controls. In the disease state of Type I diabetes mellitus, the β-cells, which are the producers of insulin and amylin, have been destroyed by an autoimmune process. Amylin has been proposed to be useful in the treatment of diabetes mellitus and hypoglycemia, including insulin-induced hypoglycemia. It has also been proposed that the coadministration of insulin with amylin is a superior therapy to the existing administration of insulin alone, and that coadministration of amylin with glucagon for the treatment of hypoglycemia is a superior therapy to the existing administration of glucagon alone. It would be useful to provide, for such purposes and others, less complicated compounds that have the activities of native human amylin, as well as compounds which may show enhanced solubility and/or stability over native human amylin. Such compounds are described and claimed herein.

SUMMARY OF THE INVENTION

The present invention is directed to novel analogues of 0the peptide hormone amylin. These compounds mimic the effects of amylin, and are referred to as amylin agonists or as agonist analogues of amylin.

The invention is also directed to pharmaceutical compositions comprising the agonist analogues of the present invention, and to methods of treatment and prevention of hypoglycemic conditions and other conditions in which enhanced amylin action is of benefit, including insulin-requiring states such as diabetes mellitus, comprising administering an agonist analogue of amylin to an animal (alone or in conjunction with an insulin or a glucagon).

DEFINITIONS

As used herein, the following terms have the following meanings unless expressly stated to the contrary:

The term "alkyl" refers to both straight- and branched-chain alkyl groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like.

The term "aryl" refers to carbocyclic aromatic groups of 6 to 14 carbon atoms such as phenyl and naphthyl, as well as heterocyclic aromatic groups containing 1 to 3 heteroatoms (nitrogen, oxygen, sulfur, etc.) such as pyridyl, triazolopyrazine, pyrimidine and the like.

The term "aralkyl" refers to an "aryl" group of 6 to 10 carbon atoms directly attached to an "alkyl" group of 1 to 4 carbon atoms and includes for example benzyl, p-chlorobenzyl, p-methylbenzyl, and 2-phenylethyl.

The term "cycloalkyl" refers to cyclic alkyl groups of 5 to 8 carbon atoms.

BRIEF DESCRIPTION OF THE DRAWINGS

FIG. 1 depicts the amino acid sequence of human amylin [SEQ. ID. NO. 1].

FIG. 2 depicts a comparison of amino acid sequences of amylins isolated from several mammals [SEQ. ID. NO. 1-6 and 42].

FIG. 3 depicts the amino acid sequence of novel amylin agonist peptides (SEQ ID NO: 43).

DETAILED DESCRIPTION OF THE INVENTION

According to the present invention, novel agonist analogues of amylin are provided. These analogues are useful as agonists of amylin, including as hyperglycemics, and may be represented by FIG. 3.

In one aspect, the present invention is directed to agonist analogues of FIG. 3, wherein $A_1$ is hydrogen Lys, Ser, Ala, des-α-amino Lys, or acetylated Lys; $B_1$ is Ala, Ser or Thr; $C_1$ is Val, Leu or Ile ; $D_1$ is His or Arg; $E_1$ is Ser or Thr; $F_1$ is Ser, Thr, Gln or Asn; $G_1$ is Asn, Gln or His; $H_1$ is Phe, Leu or Tyr; $I_1$ is Ala or Pro; $J_1$ is Ile, Val, Ala or Leu; $K_1$ is Ser, Pro, Leu, Ile or Thr; $L_1$ is Ser, Pro or Thr; $M_1$ is Asn, Asp or Gln; X and Y are independently selected residues having side chains which are chemically bonded to each other to form an intramolecular linkage; and Z is hydroxy, amino, alkylamino, dialkyiamino, cycloalkylamino, arylamino, aralkylamino, alkyloxy, aryloxy or aralkyloxy; provided that (a) when $A_1$ is Lys, $B_1$ is Ala, $C_1$ is Val, $D_1$ is His, $E_1$ is Ser, $F_1$ is Ser, $G_1$ is Asn, $H_1$ is Phe, $I_1$ is Ala, $J_1$ is Ile, $K_1$ is Ser, $L_1$ is Ser, and $M_1$ is Asn (SEQ ID NO:45); (b) when $A_1$ is Lys, $B_1$ is Ala, $C_1$ is Ile, $D_1$ is Arg, $E_1$ is Ser, $F_1$ is Ser, $G_1$ is Asn, $H_1$ is Leu, $I_1$ is Ala, $J_1$ is Ile, $K_1$ is Ser, $L_1$ is Pro, and $M_1$ is Asn (SEQ ID NO:46); (c) when $A_1$ is Lys, $B_1$ is Ala, $C_1$ is Val, $D_1$ is Arg, $E_1$ is Thr, $F_1$ is Ser, $G_1$ is Asn, $H_1$ is Leu, $I_1$ is Ala, $J_1$ is Ile, $K_1$ is Ser, $L_1$ is Pro, and $M_1$ is Asn (SEQ ID NO:47); (d) when $A_1$ is Lys, $B_1$ is Ala, $C_1$ is Val, $D_1$ is Arg, $E_1$ is Ser, $F_1$ is Ser, $G_1$ is Asn, $H_1$ is Leu, $I_1$ is Pro, $J_1$ is Val, $K_1$ is Pro, $L_1$ is Pro, and $M_1$ is Asn (SEQ ID NO:48); (e) when $A_1$ is Lys, $B_1$ is Ala, $C_1$ is Val, $D_1$ is His, $E_1$ is Ser, $F_1$ is Asn, $G_1$ is Asn, $H_1$ is Leu, $I_1$ is Pro, $J_1$ is Val, $K_1$ is Ser, $L_1$ is Pro and $M_1$ is Asn (SEQ ID NO:49); or (f) when $A_1$ is Lys, $B_1$ is Thr, $C_1$ is Val, $D_1$ is Arg, $E_1$ is Ser, $F_1$ is Ser, $G_1$ His, $H_1$ is Leu, $I_1$ is Ala, $J_1$ is Ala, $K_1$ is Leu, $L_1$ is Pro and $M_1$ is Asp (SEQ ID NO:50); then one or more of any of $A_1$ to $M_1$ is not an L-amino acid and Z is not amino.

Suitable side chains for X and Y include groups derived from alkyl sulfhydryls which may form disulfide bonds; alkyl acids and alkyl amines which may form cyclic lactams; alkyl aldehydes or alkyl halides and alkylamines which may condense and be reduced to form an alkyl amine bridge; or side chains which may be connected to form an alkyl, alkenyl, alkynyl, ether or thioether bond. Preferred alkyl chains include lower alkyl groups having from about 1 to about 6 carbon atoms.

An additional aspect of the present invention is directed to agonist analogues of FIG. 3 which are not bridged, and wherein X and Y are independently selected from Ala, Ser, Cys, Val, Leu and Ile or alkyl, aryl, or aralkyl esters and ethers of Ser or Cys.

Biologically active derivatives of the above FIG. 3 agonist analogues are also included within the scope of this invention in which the stereochemistry of individual amino acids may be inverted from (L)/S to (D)/R at one or more specific sites.

Also included within the scope of this invention are the agonist analogues modified by glycosylation of Asn, Ser and/or Thr residues.

Biologically active agonist analogues of amylin are included within the scope of this invention which contain less peptide character. Such peptide mimetics may include, for example, one or more of the following substitutions for —CO—NH—amide bonds: depsipeptides (—CO—O—), iminomethylenes (—CH$_2$—NH—), trans-alkenes (—CH=CH—), β-enaminonitriles (—C(=CH—CN)—NH—), thioamides (—CS—NH—), thiomethylenes (—S—CH$_2$— or —CH$_2$—S—), methylenes (—CH$_2$—CH$_2$—) and retro-amides (—NH—CO—).

Compounds of this invention form salts with various inorganic and organic acids and bases. Such salts include salts prepared with organic and inorganic acids, for example, HCl, HBr, H$_2$SO$_4$, H$_3$PO$_4$, trifluoroacetic acid, acetic acid, formic acid, methanesulfonic acid, toluenesulfonic acid, maleic acid, fumaric acid and camphorsulfonic acid. Salts prepared with bases include, for example, ammonium salts, alkali metal salts (such as sodium and potassium salts) and alkali earth salts (such as calcium and magnesium salts). Acetate, hydrochloride, and trifluoroacetate salts are preferred.

The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

The compounds of the invention include various stereoisomers. In the preferred compounds of this invention, the chiral centers on the peptide backbone are all S.

Compounds of the present invention may be prepared by using certain conventional coupling reactions known in the peptide art. The analogues of this invention are prepared by successively adding the desired amino acid to a growing peptide chain. Typically, an α-N-carbamoyl protected amino acid and an amino acid attached to the growing peptide chain on a resin support are reacted at room temperature in an inert solvent such as N-methylpyrrolidone, dimethylformamide or methylene chloride in the presence of coupling agents such as dicyclohexylcarbodiimide 1-hydroxybenzotriazole in the presence of a base such as diisopropylethylamine. The α-N-carbamoyl protecting group is removed from the resultant peptide with a reagent such as trifluoroacetic acid or piperidine, and the coupling reaction repeated with the next desired N-protected amino acid. Suitable N-protecting groups are known in the art, with t-butyloxycarbonyl herein preferred.

Certain preferred methods for synthesis are described in the commonly-assigned copending and commonly assigned patent application Ser. No. 667,040 ("Synthetic Preparation of Amylin and Amylin Analogs", filed Mar. 8, 1991). These methods provide for solid phase synthesis of a peptide which comprises amylin or an amylin analog which has enhanced biological activity and is substantially free of deletion and other contaminating peptides wherein said peptide is synthesized using successive synthesis cycles, whereby in each such synthesis cycle, a designated amino acid is added to a growing peptide chain attached to an insoluble resin support by formation of a peptide linkage between an α-amino group of the growing peptide chain and on α-carboxyl of the designated amino acid; and wherein each synthesis cycle comprises: (a) treating the growing peptide chain under α-amino deprotecting conditions to remove an α-amino group; (b) activating the α-carboxyl group of the α-amino protected designated amino acid; (c) contacting the growing peptide chain and the designated amino acid under coupling conditions to form a peptide linkage between the free α-amino for the peptide chain and the activated α-carboxyl of the designated amino acid; and (d) repeating steps (b) and (c) if the coupling efficiency of step (c) is less than about 97%. It is preferred to repeat steps (b) and (c) if the coupling efficiency is less than about 99%. In another preferred aspect, steps (b) and (c) are repeated in each synthesis cycle. Optionally, the coupling efficiency is measured after each coupling step.

Suitable coupling conditions include use of a solvent system which maximizes swelling of the solid support, minimizes secondary structure elements of the peptide chain during synthesis cycles, and minimizes intrapeptide and interpeptide hydrogen bonding. Preferably the synthesis cycle includes a capping step after the coupling step(s) wherein unreacted α-amino groups of the peptide chain are rendered unreactive. The synthesis cycle is successively repeated using appropriate protected α-amino acids to give amylin or an amylin analog of specified sequence. After completions of the successive synthesis cycles, said amylin or amylin analog is cleaved from the solid support. It is preferred that the cysteine residues of the peptide chain are selectively deprotected and an intramolecular disulfide bond is formed before cleaving the peptide bond from the solid support.

Suitable α-amino protective groups include t-butoxycarbonyl and 9-fluorenylmethoxycarbonyl. In one preferred aspect, when t-butoxycarbonyl is used as the α-amino protecting group, the α-carboxyl groups are activated using dicyclohexylcarbodiimide and 1-hydroxybenzotriazole to form 1-hydroxybenzotriazole esters. A particularly preferred solvent system comprises N-methylpyrrolidone.

The preparation of certain agonist analogues of amylin within the invention is described in Examples 1 to 17 herein. In addition, other agonist analogues which may be prepared according to the above procedures are set forth in Table II herein. The compounds of the invention may also be prepared using recombinant DNA techniques, using methods now known in the art. See, e.g., Sambrook et al., *Molecular Cloning: A Laboratory Manual*, 2d Ed., Cold Spring Harbor (1989).

The nomenclature of the compounds of the present invention can be used to indicate both the peptide that the sequence is based on and the modifications made to any basic peptide amylin sequence, such as human amylin. An amino acid preceded by a superscript number indicates that the named amino acid replaces the amino acid normally present at the amino acid position or the superscript in the basic amino acid sequence. For example, "$^{18}$Arg$^{25,28}$Pro-h-amylin" refers to a peptide based on the sequence of "h-amylin" or "human-amylin" having the following substitutions: Arg replacing His at residue 18, Pro replacing Ala at residue 25 and Pro replacing Ser at residue 28. The term "des-$^1$Lys-h-amylin" refers to a peptide based on the sequence of human amylin, with the first, or N-terminal, amino acid deleted.

The agonist analogues of amylin of this invention are useful in view of their pharmacological properties. In particular, compounds of this invention possess activity as amylin agonist agents, as will be evidenced by activity in the receptor binding assay and the soleus muscle assay described in Examples 18 and 19, respectively. Amylin agonist activity of compounds may also be assessed by the ability to induce hyperlactemia and/or hyperglycemia in mammals. In addition to the description of compounds pursuant to FIG. 3, certain preferred compounds are set forth in Table I. The preferred compounds des-$^1$Lys-h-amylin [SEQ. ID. NO. 7], $^{28}$Pro-h-amylin [SEQ. ID. NO. 8], $^{25,28,29}$Pro-h-amylin [SEQ. ID. NO. 9], $^{18}$Arg$^{25,28}$Pro-h-amylin [SEQ. ID. NO. 10], and des-$^1$Lys$^{18}$Arg$^{25,28}$Pro-h-amylin [SEQ. ID. NO. 11], all show amylin activity in vivo in treated test animals, provoking marked hyperlactemia followed by hyperglycemia. In addition to having activities characteristic of amylin, certain of the preferred compounds of the invention have also been found to possess more desirable solubility and stability characteristics when compared to human amylin. These preferred compounds include $^{25}$Pro$^{26}$Val$^{28,29}$Pro-h-amylin [SEQ. ID. NO. 12], $^{25,28,29}$Pro-h-amylin, and $^{18}$Arg$^{25,28}$Pro-h-amylin.

Compounds described herein which are especially preferred include $^{18}$Arg$^{25,28}$Pro-h-amylin, des-$^1$Lys$^{18}$Arg$^{25,28}$Pro-h-amylin, $^{18}$Arg$^{25,28,29}$Pro-h-amylin [SEQ. ID.

NO. 13], des-$^1$Lys$^{18}$Arg$^{25,28,29}$Pro-h-amylin [SEQ. ID. NO. 14], $^{25,28,29}$Pro-h-amylin, des-$^1$Lys$^{25,28,29}$Pro-h-amylin [SEQ. ID. NO. 15], and $^{25}$Pro$^{26}$Val$^{28,29}$Pro-h-amylin. Still further amylin agonist peptide compounds are listed in Table II. They include:

$^{23}$Leu$^{25}$Pro$^{26}$Val$^{28,29}$Pro-h-amylin [SEQ. ID. NO. 16];

$^{23}$Leu$^{25}$Pro$^{26}$Val$^{28}$Pro-h-amylin [SEQ. ID. NO. 17];

des-$^1$Lys$^{23}$Leu$^{25}$Pro$^{26}$Val$^{28}$Pro-h-amylin [SEQ. ID. NO. 18];

$^{18}$Arg$^{23}$Leu$^{25}$Pro$^{26}$Val$^{28}$Pro-h-amylin [SEQ. ID. NO. 19];

$^{18}$Arg$^{23}$Leu$^{25,28,29}$Pro-h-amylin [SEQ. ID. NO. 20];

$^{18}$Arg$^{23}$Leu$^{25,28}$Pro-h-amylin [SEQ. ID. NO. 21];

$^{17}$Ile$^{23}$Leu$^{25,28,29}$Pro-h-amylin [SEQ. ID. NO. 22];

$^{17}$Ile$^{25,28,29}$Pro-h-amylin [SEQ. ID. NO. 23];

des-$^1$Lys$^{17}$Ile$^{23}$Leu$^{25,28,29}$Pro-h-amylin [SEQ. ID. NO. 24];

$^{17}$Ile$^{18}$Arg$^{23}$Leu-h-amylin [SEQ. ID. NO. 25];

$^{17}$Ile$^{18}$Arg$^{23}$Leu$^{26}$Val$^{29}$Pro-h-amylin [SEQ. ID. NO. 26];

$^{17}$Ile$^{18}$Arg$^{23}$Leu$^{25}$Pro$^{26}$Val$^{28,\ 29Pro}$-h-amylin [SEQ. ID. NO. 27];

$^{13}$Thr$^{21}$His$^{23}$Leu$^{26}$Ala$^{28}$Leu$^{29}$Pro$^{31}$Asp-h-amylin [SEQ. ID. NO. 28];

$^{13}$Thr$^{21}$His$^{23}$Leu$^{26}$Ala$^{29}$Pro$^{31}$Asp-h-amylin [SEQ. ID. NO. 29];

Des-1Lys13Thr21His23Leu26Ala28Pro31Asp-h-amylin [SEQ. ID. NO. 30];

$^{13}$Thr$^{18}$Arg$^{21}$His$^{23}$Leu$^{26}$Ala$^{29}$Pro$^{31}$Asp-h-amylin [SEQ. ID. NO. 31];

$^{13}$Thr$^{18}$Arg$^{21}$His$^{23}$Leu$^{28,29}$Pro$^{31}$Asp-h-amylin [SEQ. ID. NO. 32]; and, $^{13}$Thr$^{18}$Arg$^{21}$His$^{23}$Leu$^{25}$Pro$^{26}$Ala$^{28,29}$Pro$^{31}$Asp-h-amylin [SEQ. ID. NO. 33].

The compounds of this invention can be combined with pharmaceutical carriers to prepare pharmaceutical forms suitable for parenteral administration. Experimental responses of the compounds support the clinical application of such pharmaceutical compositions in the treatment of diabetes mellitus and other insulin-requiring states, as well as in the prevention and treatment of episodes of hypoglycemia. The compounds of this invention can also be combined with insulin for the treatment of diabetes mellitus and other insulin-requiring states. By "insulin" is meant a polypeptide or its equivalent useful in regulation of blood glucose levels. A general description of such insulins is provided in *Goodman and Gilman's The Pharmacological Basis of Therapeutics*, 8th Ed., Pergamon Press (1990). Such insulins can be fast acting, intermediate acting, or long acting. Various derivatives of insulin exist and are useful in this invention. See, e.g., U.S. Pat. Nos. 5,049,547, 5,028, 587, and 5,016,643. Insulin peptides are also useful (see, e.g., U.S. Pat. No. 5,008,241), as are analogues (see, e.g., U.S. Pat. Nos. 4,992,417 and 4,992,418). Such compositions can be administered by any standard route, including nasal administration (see, e.g., U.S. Pat. Nos. 4,988,512 and 4,985,242, and 2 *BioWorld Today*, No. 125 (1991)). The compounds of this invention are also useful in combination with a glucagon for the prevention and treatment of hypoglycemia. See Young et al. U.S. application Ser. No. 07/640,478, filed Jan. 10, 1991, entitled "Hyperglycemic Compositions," which is incorporated herein by reference.

Compositions or products of the invention may conveniently be provided in the form of solutions suitable for parenteral (including intravenous, intramuscular and subcutaneous) or nasal or oral administration. In many cases, it will be convenient to provide an agonist analogue of amylin and an insulin or glucagon in a single composition or solution for administration together. In other cases, it may be more advantageous to administer an insulin or a glucagon separately from said agonist analogue. A suitable administration format may best be determined by a medical practitioner for each patient individually. Suitable pharmaceutically acceptable carriers and their formulation are described in standard formulation treatises, e.g., *Remington's Pharmaceutical Sciences* by E. W. Martin. See also Wang, Y. J. and Hanson, M. A. "Parenteral Formulations of Proteins and Peptides: Stability and Stabilizers," *Journal of Parenteral Science and Technology*, Technical Report No. 10, Supp. 42:2S (1988). Suitable formulations including insulin or glucagon are known in the art.

The agonist preparations of the invention may be stabilized at neutral pH. Since the products of the invention are amphoteric they may be utilized as free bases, as acid addition salts or as metal salts. The salts must, of course, be pharmaceutically acceptable, and these will include metal salts, particularly alkali and alkaline earth metal salts, e.g., potassium or sodium salts. A wide variety of pharmaceutically acceptable acid addition salts are available, as described above. These include those prepared from both organic and inorganic acids, preferably mineral acids. Typical acids which may be mentioned by way of example include citric, succinic, lactic, hydrochloric and hydrobromic acids. Such products are readily prepared by procedures well known to those skilled in the art.

The products of the invention will normally be provided as parenteral compositions for injection or infusion. They can, for example, be suspended in an inert oil, suitably a vegetable oil such as sesame, peanut, or olive oil. Alternatively, they can be suspended in an aqueous isotonic buffer solution at a pH of about 5.6 to 7.4. Useful buffers include sodium citrate-citric acid and sodium phosphate-phosphoric acid. A form of repository or "depot" slow release preparation may be used so that therapeutically effective amounts of the preparation are delivered into the bloodstream over many hours or days following transdermal injection.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions.

If desired, solutions of the above compositions may be thickened with a thickening agent such as methylcellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

The therapeutically useful compositions of the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of an agonist compound with or without insulin or glucagon which will be effective in one or multiple doses to control or reestablish blood sugar at the selected level. Therapeutically effective amounts of an agonist analogue of amylin as described herein for the treatment of hypoglycemia are those that increase blood sugar levels, preferably to above 80 mg/dl. Therapeutically effective amounts of such agonist analogues for the treatment of diabetes mellitus and other insulin-requiring states are those sufficient to provide for reduced incidence of insulin overdose or undesired hypoglycemia. As will be recognized by those in the field, an effective amount of therapeutic agent will vary with many factors including the age and weight of the patient, the patient's physical condition, the blood sugar level to be obtained, and other factors. Typical dosage units for treatment of diabetes mellitus will contain from about 0.1 to 5 mg of an amylin agonist compound and, if desired, about 0.5 to about 10 mg of an insulin. Typical dosage units for the treatment of hypoglycemia will contain about 0.5 to 1.0 mg of an amylin agonist compound and, if desired, the art recognized quantity, or less, of a glucagon.

As set forth above, compositions useful in the invention are formulated by standard procedure. These compositions are also administered by standard procedure. Suitable doses are readily determined by those in the art, examples of which are provided above.

To assist in understanding the present invention, the following examples are included which describe the results of a series of experiments. The following examples relating to this invention should not, of course, be construed as specifically limiting the invention. Such variations of the invention, now known or later developed, which would be within the purview of one skilled in the art are considered to fall within the scope of the present invention as hereinafter claimed.

EXAMPLES

Example 1

Preparation of $^{28}$Pro-human-Amylin [SEQ. ID. NO. 8]

Solid phase synthesis of this analogue of human ("h-") amylin using methylbenzhydrylamine anchor-bond resin and $N^a$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid hydrofluoric acid ("HF") in the presence of dimethylsulfide and anisole. The $^{23}$Pro-h-amylin was purified by preparative HPLC. The peptide was found to be homogeneous by analytical HPLC and capillary electrophoresis and the structure confirmed by amino acid analysis and sequence analysis. The product gave the desired mass ion. FAB mass spec: (M+1)/e=3914.

Example 2

Preparation of $^{25}$Pro$^{26}$Val$^{28,29}$Pro-h-Amylin [SEQ. ID. NO. 12]

Solid phase synthesis of this amylin analogue using methylbenzhydrylamine anchor-bond resin and $N^a$-Boc/benzyl-side chain protection was carried out by standard peptide synthesis methods. The $^{2,7}$-[disulfide]amylin-MBHA-resin was obtained by treatment with thallium (III) trifluoroacetate in trifluoroacetic acid. After cyclization was achieved the resin and side chain protecting groups were cleaved with liquid HF in the presence of dimethylsulfide and anisole. The $^{25}$Pro$^{26}$Val$^{28,29}$Pro-h-amylin was purified by preparative HPLC. The peptide was found to be homogeneous by analytical HPLC and capillary electrophoresis and the structure confirmed by amino acid analysis and sequence analysis. The product gave the desired mass ion. FAB mass spec: (M+1)/e=3936.

Example 3

Preparation of $^{2,7}$Cyclo-[$^{2}$Asp,$^{7}$Lys]-h-Amylin [SEQ. ID. NO. 34]

Solid phase synthesis of this amylin analogue using methylbenzhydrylamine anchor-bond resin and $N^a$-Boc/benzyl-side chain protection was carried out by standard peptide synthesis methods. $^{2}$Asp and $^{7}$Lys were introduced with Boc-$^{2}$Asp(Fmoc)-OH and Boc-$^{7}$Lys(Fmoc)-OH. Following selective side-chain deprotection with piperidine the side-chain to side-chain ($^{2}$Asp-$^{7}$Lys) cyclization was carried out using Benzotriazol-1yl-oxy-tris(dimethylamino)-phosphonium hexafluorophosphate (BOP reagent). Cyclization was as described in Di Maio, J., et al,. *J. Med. Chem.* 33:661-667 (1990); Felix, A. M., et al., *Int J. Pest. Prot. Res.* 32:441 (1988). The $^{2,7}$cyclo-[$^{2}$Asp,$^{7}$Lys]amylin-MBHA-resin obtained after cyclization was cleaved, with liquid HF in the presence of dimethylsulfide and anisole. The $^{2,7}$cyclo-[$^{2}$Asp,$^{7}$Lys]-h-amylin was purified by preparative HPLC. The peptide was found to be homogeneous by analytical HPLC and capillary electrophoresis and the structure confirmed by amino acid analysis and sequence analysis. FAB mass spec: (M+1)/e=3925.

Example 4

Preparation of des-$^{1}$Lys-h-Amylin [SEQ. ID. NO. 7]

Solid phase synthesis of des-$^{1}$Lys-h-amylin (also represented as $^{2-37}$h-amylin) using methylbenzhydrylamine anchor-bond resin and $N^a$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The des-$^{1}$Lys-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: (M+H)$^{+}$=3,775.

Example 5

Preparation of $^{1}$Ala-h-Amylin [SEQ. ID. NO. 35]

Solid phase synthesis of $^{1}$Ala-h-amylin using methylbenzhydrylamine anchor-bond resin and $N^a$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The $^{1}$Ala-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: $(M+H)^+=3,847$.

Example 6

Preparation of $^1$Ser-h-Amylin [SEQ. ID. NO. 36]

Solid phase synthesis of $^1$Ser-h-amylin using methylbenzhydrylamine anchor-bond resin and $N^\alpha$-Boc/benzyl-side chain protection was carried out by standard peptide synthesis methods. The $^{2,7}$-[disulfide]amylin-MBLA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The $^1$Ser-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: $(M+H)^+=3,863$.

Example 7

Preparation of $^{29}$Pro-h-Amylin [SEQ. ID. NO. 37]

Solid phase synthesis of this analogue of human amylin using methylbenzhydrylamine anchor-bond resin and $N^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid RF in the presence of dimethylsulfide and anisole. The $^{29}$Pro-h-amylin was purified by preparative HPLC. The peptide was found to be homogeneous by analytical HPLC and capillary electrophoresis and the structure confirmed by amino acid analysis and sequence analysis. The product gave the desired mass ion. FAB mass spec: $(M+H)^+=3916$.

Example 8

Preparation of $^{25,28}$Pro-h-Amylin [SEQ. ID. NO. 38]

Solid phase synthesis of $^{25,28}$Pro-h-amylin using methylbenzhydrylamine anchor-bond resin and $N^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The $^{25,28}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: $(M+H)^+=3,939$.

Example 9

Preparation of des-$^1$Lys$^{25,28}$Pro-h-Amylin [SEQ. ID. NO. 39]

Solid phase synthesis of des-$^1$Lys$^{25,28}$Pro-h-amylin using methylbenzhydrylamine anchor-bond resin and $N^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The des-$^1$Lys$^{25,28}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: $(M+H)^+=3,811$.

Example 10

Preparation of $^{18}$Arg$^{25,28}$Pro-h-Amylin [SEQ. ID. NO. 10]

Solid phase synthesis of $^{18}$Arg$^{25,28}$Pro-h-amylin using methylbenzhydrylamine anchor-bond resin and $N^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The $^{18}$Arg$^{25,28}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: $(M+H)^+=3,959$.

Example 11

Preparation of des-$^1$Lys$^{18}$Arg$^{25,28}$Pro-h-Amylin [SEQ. ID. NO. 11]

Solid phase synthesis of des-$^1$Lys$^{18}$Arg$^{25,28}$Pro-h-amylin using methylbenzhydrylamine anchor-bond resin and $N^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The des-$^1$Lys$^{18}$Arg$^{25,28}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: $(M+H)^+=3,832$.

Example 12

Preparation of $^{18}$Arg$^{25,28,29}$Pro-h-Amylin [SEQ. ID. NO. 13]

Solid phase synthesis of $^{18}$Arg$^{25,28,29}$Pro-h-amylin using methylbenzhydrylamine anchor-bond resin and N$^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The $^{18}$Arg$^{25,28,29}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: (M+H)$^+$=3,971.

Example 13

Preparation of des-$^1$Lys$^{18}$Arg$^{25,28,29}$Pro-h-Amylin [SEQ. ID. NO. 14]

Solid phase synthesis of des-$^1$Lys$^{18}$Arg$^{25,28,29}$Pro-h-amylin using methylbenzhydrylamine anchor-bond resin and N$^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The des-$^1$Lys$^{18}$Arg$^{25,28,29}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: (M+H)$^+$=3,843.

Example 14

Preparation of $^{25,28,29}$Pro-h-Amylin [SEQ. ID. NO. 9]

Solid phase synthesis of $^{25,28,29}$Pro-h-amylin using methylbenzhydrylamine anchor-bond resin and N$^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The $^{25,28,29}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: (M+H)$^+$=3,949.

Example 15

Preparation of des-$^1$Lys$^{25,28,29}$Pro-h-Amylin [SEQ. ID. NO. 15]

Solid phase synthesis of des-$^1$Lys$^{25,28,29}$Pro-h-amylin using methylbenzhydrylamine anchor-bond resin and N$^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The des-$^1$Lys$^{25,28,29}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: (M+H)$^+$=3,823.

Example 16

Preparation of des-$^1$Lys$^{25}$Pro$^{26}$Val$^{28,29}$Pro-h-Amylin [SEQ. ID. NO. 40]

Solid phase synthesis of this h-amylin analogue using methylbenzhydrylamine anchor-bond resin and N$^\alpha$-Boc/benzyl-side chain protection is carried out by standard peptide synthesis methods, and the $^{2,7}$-[disulfide]amylin-MBHA-resin obtained by treatment with thallium (III) trifluoroacetate in trifluoroacetic acid. After cyclization is achieved the resin and side chain protecting groups are cleaved with liquid HF in the presence of dimethylsulfide and anisole. The des-$^1$Lys$^{25}$Pro$^{26}$Val$^{28,29}$Pro-h-amylin is then purified by preparative HPLC.

Example 17

Preparation of [(D)-$^{11}$Arg]-Amylin [SEQ. ID. NO. 41]

Solid phase synthesis of this amylin analogue using methylbenzhydrylamine anchor-bond resin and N$^\alpha$-Boc/benzyl-side chain protection is carried out by standard peptide synthesis methods. (D)-$^{11}$Arg is introduced with Boc-(D)-$^{11}$Arg(Mtr)-OH. The $^{2,7}$-[disulfide]amylin-MBHA-resin, obtained by treatment with thallium (III) trifluoroacetate in trifluoroacetic acid, is cyclized and the resin and side chain protecting groups are cleaved with, liquid HF in the presence of dimethylsulfide and anisole. The [(D)-$^{11}$Arg]-amylin is then purified by preparative HPLC.

Example 18

Receptor Binding Assay

Evaluation of the binding of compounds of the invention to amylin receptors was carried out as follows. $^{125}$I-rat amylin (Bolton-Hunter labeled at the N-terminal lysine) was purchased from Amersham Corporation (Arlington Heights, Ill.). Specific activities at time of use ranged from 1950 to 2000 Ci/mmol. Unlabeled peptides were obtained from BACHEM Inc. (Torrance, Calif.) and Peninsula Laboratories (Belmont, Calif.).

Male Sprague-Dawley rats (200-250) grams were sacrificed by decapitation. Brains were removed to cold phosphate-buffered saline (PBS). From the ventral surface, cuts were made rostral to the hypothalamus, bounded laterally by the olfactory tracts and extending at a 45E angle medially from these tracts. This basal forebrain tissue, containing the nucleus accumbens and surrounding regions, was weighed and homogenized in ice-cold 20 mM HEPES buffer (20 mM HEPES acid, pH adjusted to 7.4 with NaOH at 23EC). Membranes were washed three times in fresh buffer by centrifugation for 15 minutes at 48,000×g. The final membrane pellet was resuspended in 20 mM HEPES buffer containing 0.2 mM phenylmethylsulfonyl fluoride (PMSF).

To measure $^{125}$I-amylin binding, membranes from 4 mg original wet weight of tissue were incubated with $^{125}$I-amylin at 12-16 pM in 20 mM HEPES buffer containing 0.5 mg/ml bacitracin, 0.5 mg/ml bovine serum albumin, and 0.2 mM PMSF. Solutions were incubated for 60 minutes at 23EC. Incubations were terminated by filtration through GF/B glass fiber filters (Whatman Inc., Clifton, N.J.) which had been presoaked for 4 hours in 0.3% poylethyleneimine in order to reduce nonspecific binding of radiolabeled peptides. Filters were washed immediately before filtration with 5 ml cold PBS, and immediately after filtration with 15 ml cold PBS. Filters were removed and radioactivity assessed in a gamma-counter at a counting efficiency of 77%. Competition curves were generated by measuring binding in the presence of $10^{-12}$ to $10^{-6}$ M unlabeled test compound and were analyzed by nonlinear regression using a 4-parameter logistic equation (Inplot program; GraphPAD Software, San Diego).

In this assay, purified human amylin binds to its receptor at a measured $IC_{50}$ of about 50 pM. Results for test compounds of the invention are set forth in Table I, showing that each of the compounds has significant receptor binding activity.

Example 19

Soleus Muscle Assay

Evaluation of the amylin agonist activity of compounds of the invention was carried out using the soleus muscle assay as follows. Male Harlan Sprague-Dawley rats of approximately 200 g mass were used in order to maintain mass of the split soleus muscle less than 40 mg. The animals were fasted for 4 hours prior to sacrifice by decapitation. The skin was stripped from the lower limb which was then pinned out on corkboard. The tendo achilles was cut just above os calcis and m. gastrocnemius reflected out from the posterior aspect of the tibia. M. soleus, a small 15-20 mm long, 0.5 mm thick flat muscle on the bone surface of m. gastrocnemius was then stripped clear and the perimysium cleaned off using fine scissors and forceps. M. soleus was then split into equal parts using a blade passed antero-posteriorly through the belly of the muscle to obtain a total of 4 muscle strips from each animal. After dissecting the muscle from the animal, it was kept for a short period in physiological saline. It was not necessary that the muscle be held under tension as this had no demonstrable effects on radioglucose incorporation into glycogen.

Muscles were added to 50 mL Erlenmeyer flasks containing 10 mL of a pregassed Krebs-Ringer bicarbonate buffer containing (each liter) NaCl 118.5 mmol (6.93 g), KCl 5.94 mmol (443 mg), $CaCl_2$ 2.54 mmol (282 mg), $MgSO_4$ 1.19 mmol (143 mg), $KH_2PO_4$ 1.19 mmol (162 mg), $NaHCO_3$ 25 mmol (2.1 g), 5.5 mmol glucose (1 g) and recombinant human insulin (Humulin-R, Eli Lilly, IN) and the test compound, as detailed below. pH at 37EC was verified as being between 7.1 and 7.4. Muscles were assigned to different flasks so that the 4 muscle pieces from each animal were evenly distributed among the different assay conditions. The incubation media were gassed by gently blowing carbogen (95% $O_2$, 5% $CO_2$) over the surface while being continuously agitated at 37EC in an oscillating water bath. After a half-hour "preincubation" period, 0.5 µCi of U-$^{14}$C-glucose was added to each flask which was incubated for a further 60 minutes. Each muscle piece was then rapidly removed, blotted and frozen in liquid $N_2$, weighed and stored for subsequent determination of $^{14}$C-glycogen.

$^{14}$C-glycogen determination was performed in a 7 mL scintillation vial. Each frozen muscle specimen was placed in a vial and digested in 1 mL 60% potassium hydroxide at 70 EC for 45 minutes under continuous agitation. Dissolved glycogen was precipitated out onto the vial by the addition of 3 mL absolute ethanol and overnight cooling at −20 EC. The supernatant was gently aspirated, the glycogen washed again with ethanol, aspirated and the precipitate dried under vacuum. All ethanol is evaporated to avoid quenching during scintillation counting. The remaining glycogen was redissolved in 1 mL water and 4 mL scintillation fluid and counted for $^{14}$C.

The rate of glucose incorporation into glycogen (expressed in µmol/g/hr) was obtained from the specific activity of $^{14}$C-glucose in the 5.5 mM glucose of the incubation medium, and the total $^{14}$C counts remaining in the glycogen extracted from each muscle. Dose/response curves were fitted to a 4-parameter logistic model using a least-squares iterative routine (ALLFIT, v2.7, NIH, MD) to derive $EC_{50}$'s. Since $EC_{50}$ is log-normally distributed, it is expressed ∀ standard error of the logarithm. Pairwise comparisons were performed using t-test based routines of SYSTAT (Wilkinson, "SYSTAT: the system for statistics," SYSTAT Inc., Evanston Ill. (1989)).

Dose response curves were generated with muscles added to media containing 7.1 nM (1000 µU/mL) insulin and each test compound added at final (nominal) concentrations of 0, 1, 3, 10, 30, 100, 300 and 1000 nM. Each assay also contained internal positive controls consisting of a single batch of archived rat amylin, lyophilized and stored at −70 EC.

Human amylin is a known hyperglycemic peptide, and $EC_{50}$ measurements of amylin preparations in the soleus muscle assay range typically from about 1-10 nM, although some commercial preparations which are less than 90% pure have higher $EC_{50}$'s due to the presence of contaminants that result in a lower measured activity. Results for test compounds are set forth in Table I, showing that each of the compounds has amylin activity.

TABLE I

| | | Receptor Binding Assay $IC_{50}$ (pM) | Soleus Muscle Assay $EC_{50}$ (nM) |
|---|---|---|---|
| 1) | $^{28}$Pro-h-Amylin | 15.0 | 2.64 |
| 2) | $^{25}$Pro$^{26}$Val$^{28,29}$Pro-h-Amylin | 18.0 | 4.68 |
| 3) | $^{2,7}$Cyclo-[$^2$Asp, $^7$Lys]-h-Amylin | 310.0 | 6.62 |
| 4) | $^{2-37}$h-Amylin | 236.0 | 1.63 |
| 5) | $^1$Ala-h-Amylin | 148.0 | 12.78 |
| 6) | $^1$Ser-h-Amylin | 33.0 | 8.70 |
| 7) | $^{29}$Pro-h-Amylin | 64.0 | 3.75 |
| 8) | $^{25,28}$Pro-h-Amylin | 26.0 | 13.20 |
| 9) | des-$^1$Lys$^{25,28}$Pro-h-Amylin | 85.0 | 7.70 |
| 10) | $^{18}$Arg$^{25,28}$Pro-h-Amylin | 32.0 | 2.83 |
| 11) | des-$^1$Lys$^{18}$Arg$^{25,28}$Pro-h-Amylin | 82.0 | 3.77 |
| 12) | $^{18}$Arg$^{25,28,29}$Pro-h-Amylin | 21.0 | 1.25 |

TABLE I-continued

|  | Receptor Binding Assay IC$_{50}$ (pM) | Soleus Muscle Assay EC$_{50}$ (nM) |
|---|---|---|
| 13) des-$^1$Lys$^{18}$Arg$^{25,28,29}$Pro-h-Amylin | 21.0 | 1.86 |
| 14) $^{25,28,29}$Pro-h-Amylin | 10.0 | 3.71 |
| 15) des-$^1$Lys$^{25,28,29}$Pro-h-Amylin | 14.0 | 4.15 |

TABLE II

| | A$_1$ | B$_1$ | C$_1$ | D$_1$ | E$_1$ | F$_1$ | G$_1$ | H$_1$ | I$_1$ | J$_1$ | K$_1$ | L$_1$ | M$_1$ | Z |
|---|---|---|---|---|---|---|---|---|---|---|---|---|---|---|
| 18) | Lys | Ala | Val | His | Ser | Ser | Asn | Leu | Pro | Val | Pro | Pro | Asn | -NH$_2$ |
| 19) | Lys | Ala | Val | His | Ser | Ser | Asn | Leu | Pro | Val | Pro | Ser | Asn | -NH$_2$ |
| 20) | Hydrogen | Ala | Val | His | Ser | Ser | Asn | Leu | Pro | Val | Pro | Ser | Asn | -NH$_2$ |
| 21) | Lys | Ala | Val | Arg | Ser | Ser | Asn | Leu | Pro | Val | Pro | Ser | Asn | -NH$_2$ |
| 22) | Lys | Ala | Val | Arg | Ser | Ser | Asn | Leu | Pro | Ile | Pro | Pro | Asn | -NH$_2$ |
| 23) | Lys | Ala | Val | Arg | Ser | Ser | Asn | Leu | Pro | Ile | Pro | Ser | Asn | -NH$_2$ |
| 24) | Lys | Ala | Ile | His | Ser | Ser | Asn | Leu | Pro | Ile | Pro | Pro | Asn | -NH$_2$ |
| 25) | Lys | Ala | Ile | His | Ser | Ser | Asn | Phe | Pro | Ile | Pro | Pro | Asn | -NH$_2$ |
| 26) | Hydrogen | Ala | Ile | His | Ser | Ser | Asn | Leu | Pro | Ile | Pro | Pro | Asn | -NH$_2$ |
| 27) | Lys | Ala | Ile | Arg | Ser | Ser | Asn | Leu | Ala | Ile | Ser | Ser | Asn | -NH$_2$ |
| 28) | Lys | Ala | Ile | Arg | Ser | Ser | Asn | Leu | Ala | Val | Ser | Pro | Asn | -NH$_2$ |
| 29) | Lys | Ala | Ile | Arg | Ser | Ser | Asn | Leu | Pro | Val | Pro | Pro | Asn | -NH$_2$ |
| 30) | Lys | Thr | Val | His | Ser | Ser | His | Leu | Ala | Ala | Leu | Pro | Asp | -NH$_2$ |
| 31) | Lys | Thr | Val | His | Ser | Ser | His | Leu | Ala | Ala | Ser | Pro | Asp | -NH$_2$ |
| 32) | Hydrogen | Thr | Val | His | Ser | Ser | His | Leu | Ala | Ala | Pro | Ser | Asp | -NH$_2$ |
| 33) | Lys | Thr | Val | Arg | Ser | Ser | His | Leu | Ala | Ala | Ser | Pro | Asp | -NH$_2$ |
| 34) | Lys | Thr | Val | Arg | Ser | Ser | His | Leu | Ala | Ile | Pro | Pro | Asp | -NH$_2$ |
| 35) | Lys | Thr | Val | Arg | Ser | Ser | His | Leu | Pro | Ala | Pro | Pro | Asp | -NH$_2$ |

We claim:

1. An agonist analog of amylin having the sequence des-$^1$Lys$^{25}$Pro$^{26}$Val$^{28,29}$Pro-h-amylin (SEQ ID NO: 40).

2. The agonist analog of amylin of claim 1 as an acetate salt.

3. A method of treating diabetes mellitus in a mammal comprising administering the agonist analog of amylin of claim 2 to the mammal.

4. The agonist analog of amylin of claim 1 as a hydrochloride salt.

5. A method of treating diabetes mellitus in a mammal comprising administering the agonist analog of amylin of claim 1 to the mammal.

6. The method of claim 5 further comprising administration of insulin.

7. An agonist analog of amylin having the amino acid sequence of (SEQ ID NO: 44) $^1$A$_1$-X-Asn-Thr-$^5$Ala-Thr-Y-Ala-Thr-$^{10}$Gln-Arg-Leu-B$_1$-Asn-$^{15}$Phe-Leu-C$_1$-D$_1$-E$_1$-$^{20}$F$_1$-G$_1$-Asn-H$_1$-Gly-$^{25}$I$_1$-J$_1$-Leu-K$_1$-L$_1$$^{30}$Thr-M$_1$-Val-Gly-Ser-$^{35}$Asn-Thr-Tyr-Z, wherein A$_1$ is Lys, Ala, Ser or hydrogen,
B$_1$ is Ala, Ser or Thr;
C$_1$ is Val, Leu or Ile;
D$_1$ is His or Arg;
E$_1$ is Ser or Thr;
F$_1$ is Ser, Thr, Gln or Asn;
G$_1$ is Asn, Gln or His;
H$_1$ Phe, Leu or Tyr;
I$_1$ is Ala or Pro;
J$_1$ is Ile, Val, Ala or Leu;
K$_1$ is Ser, Pro, Leu, Ile or Thr;
L$_1$ is Ser, Pro or Thr;
M$_1$ is Asn, Asp, or Gln;
X and Y are independently selected residues having side chains which are chemically bonded to each other to form an intramolecular linkage; and
Z is hydroxy, amino, alkylamino, dialkylamino, cycloalkylamino, arylamino, aralkylamino, alkyloxy, aryloxy or aralkyloxy; and provided that when (a) A$_1$ is Lys, B$_1$ is Ala, C$_1$ is Val, D$_1$ is His, E$_1$ is Ser, F$_1$ is Ser, G$_1$ is Asn, H$_1$ is Phe, I$_1$ is Ala, J$_1$ is Ile, K$_1$ is Ser, L$_1$ is Ser, and M$_1$ is Asn (SEQ ID NO: 45);
(b) A$_1$ is Lys, B$_1$ is Ala, C$_1$ is Ile, D$_1$ is Arg, E$_1$ is Ser, F$_1$ is Ser, G$_1$ is Asn, H$_1$ is Leu, I$_1$ is Ala, J$_1$ is Ile, K$_1$ is Ser, L$_1$ is Pro, and M$_1$ is Asn (SEQ ID NO: 46);
(c) A$_1$ is Lys, B$_1$ is Ala, C$_1$ is Val, D$_1$ is Arg, E$_1$ is Thr, F$_1$ is Ser, G$_1$ is Asn, H$_1$ is Leu, I$_1$ is Ala, J$_1$ is Ile, K$_1$ is Ser, L$_1$ is Pro, and M$_1$ is Asn (SEQ ID NO: 47);
(d) A$_1$ is Lys, B$_1$ is Ala, C$_1$ is Val, D$_1$ is Arg, E$_1$ is Ser, F$_1$ is Ser, G$_1$ is Asn, H$_1$ is Leu, I$_1$ is Pro, J$_1$ is Val, K$_1$ is Pro, L$_1$ is Pro and M$_1$ is Asn (SEQ ID NO: 48);
(e) A$_1$ is Lys, B$_1$ is Ala, C$_1$ is Val, D$_1$ is His, E$_1$ is Ser, F$_1$ is Asn, G$_1$ Asn, H$_1$ is Leu, I$_1$ is Pro, J$_1$ is Val, K$_1$ is Ser, L$_1$ is Pro, and M$_1$ is Asn (SEQ ID NO: 49); or
(f) A$_1$ is Lys, B$_1$ is Thr, C$_1$ is Val, D$_1$ is Arg, E$_1$ is Ser, F$_1$ is Ser, G$_1$ His, H$_1$ is Leu, I$_1$ is Ala, J$_1$ is Ala, K$_1$ is Leu, L$_1$ is Pro, and M$_1$ is Asp (SEQ ID NO: 50);
then one or more of any of A$_1$ to M$_1$ is a D-amino acid and Z is not amino; as a salt.

8. The agonist analog of amylin of claim 7 as an acetate salt.

9. A method of treating diabetes mellitus in a mammal comprising administering the agonist analog of amylin of claim 8 to the mammal.

10. The method of claim 9 wherein the diabetes mellitus is type I diabetes.

11. The method of claim 9 wherein the diabetes mellitus is insulin-requiring type II diabetes.

12. A method of treating diabetes mellitus in a mammal comprising administering the agonist analog of amylin of claim 7 to the mammal.

13. The method of claim 12 further comprising administration of insulin.

14. The method of claim 12 wherein the diabetes mellitus is type I diabetes.

15. The method of claim 12 wherein the diabetes mellitus is insulin-requiring type II diabetes.

16. The method of claim 12 wherein the agonist analog of amylin is given by intravenous, intramuscular, nasal, oral, or transdermal administration.

17. A composition comprising a therapeutically effective amount of the agonist analog of amylin of claim 7 and insulin.

18. A method of treating diabetes mellitus in a mammal comprising administering the composition of claim 17.

19. The method of claim 18 wherein the composition is given by intravenous, intramuscular, nasal, oral or transdermal administration.

* * * * *

SEQUENCE LISTING (1) GENERAL INFORMATION:

(iii) NUMBER OF SEQUENCES: 41

(2) INFORMATION FOR SEQ ID NO: 1:

(i) SEQUENCE CHARACTERISTICS:
      (A) LENGTH: 37 amino acids
      (B) TYPE: amino acid
      (C) STRANDEDNESS: single
      (D) TOPOLOGY: linear (ii) MOLECULE TYPE: peptide (ix) FEATURE:
      (B) LOCATION: 37
      (D) OTHER INFORMATION: amidated Tyr (Tyrosinamide)

(xi) SEQUENCE DESCRIPTION: SEQ ID NO: 1:

```
Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35
```

(2) INFORMATION FOR SEQ ID NO: 2:

(i) SEQUENCE CHARACTERISTICS:
      (A) LENGTH: 37 amino acids

```
            (B) TYPE: amino acids
            (C) STRANDEDNESS: single
            (D) TOPOLOGY: linear (ii) MOLECULE TYPE: peptide (ix) FEATURE:
            (B) LOCATION: 37
            (D) OTHER INFORMATION: amidated Tyr (Tyrosinamide)

(xi) SEQUENCE DESCRIPTION: SEQ ID NO: 2:

Lys Cys Asn Thr Ala Thr Cys Ala Thr Gln Arg Leu Ala Asn Phe Leu
1               5                   10                  15

Ile Arg Ser Ser Asn Asn Leu Gly Ala Ile Leu Ser Pro Thr Asn Val
            20                  25                  30

Gly Ser Asn Thr Tyr
            35

(2) INFORMATION FOR SEQ ID NO: 3:

(i) SEQUENCE CHARACTERISTICS:
            (A) LENGTH: 37 amino acids
            (B) TYPE: amino acid
            (C) STRANDEDNESS: single
            (D) TOPOLOGY: linear (ii) MOLECULE TYPE: peptide (ix) FEATURE:
            (B) LOCATION: 37
            (D) OTHER INFORMATION: amidated Tyr (Tyrosinamide)

(xi) SEQUENCE DESCRIPTION: SEQ ID NO: 3:

Lys Cys Asn Thr Ala Thr Cys Ala Thr Gln Arg Leu Ala Asn Phe Leu
1               5                   10                  15

Val Arg Thr Ser Asn Asn Leu Gly Ala Ile Leu Ser Pro Thr Asn Val
            20                  25                  30

Gly Ser Asn Thr Tyr
            35

(2) INFORMATION FOR SEQ ID NO: 4:

(i) SEQUENCE CHARACTERISTICS:
            (A) LENGTH: 37 amino acids
            (B) TYPE: amino acid
            (C) STRANDEDNESS: single
            (D) TOPOLOGY: linear (ii) MOLECULE TYPE: peptide (ix) FEATURE:
            (B) LOCATION: 37
            (D) OTHER INFORMATION: amidated Tyr (Tyrosinamide)

(xi) SEQUENCE DESCRIPTION: SEQ ID NO: 4:

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Asn Val
            20                  25                  30

Gly Ser Asn Thr Tyr
            35

(2) INFORMATION FOR SEQ ID NO: 5:

(i) SEQUENCE CHARACTERISTICS:
            (A) LENGTH: 37 amino acids
            (B) TYPE: amino acid
```

-continued

```
            (C) STRANDEDNESS: single
            (D) TOPOLOGY: linear (ii) MOLECULE TYPE: peptide (ix) FEATURE:
            (B) LOCATION: 37
            (D) OTHER INFORMATION: amidated Tyr (Tyrosinamide)

(xi) SEQUENCE DESCRIPTION: SEQ ID NO: 5:

Lys Cys Asn Thr Ala Thr Cys Ala Thr Gln Arg Leu Ala Asn Phe Leu
1               5                   10                  15

Val His Ser Asn Asn Asn Leu Gly Pro Val Leu Ser Pro Thr Asn Val
                20                  25                  30

Gly Ser Asn Thr Tyr
            35

(2) INFORMATION FOR SEQ ID NO: 6:

(i) SEQUENCE CHARACTERISTICS:
            (A) LENGTH: 37 amino acids
            (B) TYPE: amino acid
            (C) STRANDEDNESS: single
            (D) TOPOLOGY: linear (ii) MOLECULE TYPE: peptide (ix) FEATURE:
            (B) LOCATION: 37
            (D) OTHER INFORMATION: amidated Tyr (Tyrosinamide)

(xi) SEQUENCE DESCRIPTION: SEQ ID NO: 6:

Lys Cys Asn Thr Ala Thr Cys Ala Thr Gln Arg Leu Thr Asn Phe Leu
1               5                   10                  15

Val Arg Ser Ser His Asn Leu Gly Ala Ala Leu Leu Pro Thr Asp Val
                20                  25                  30

Gly Ser Asn Thr Tyr
            35

(2) INFORMATION FOR SEQ ID NO: 7:

(i) SEQUENCE CHARACTERISTICS:
            (A) LENGTH: 36 amino acids
            (B) TYPE: amino acid
            (C) STRANDEDNESS: single
            (D) TOPOLOGY: linear (ii) MOLECULE TYPE: peptide (ix) FEATURE:
            (B) LOCATION: 36
            (D) OTHER INFORMATION: amidated Tyr (Tyrosinamide)

(xi) SEQUENCE DESCRIPTION: SEQ ID NO: 7:

Cys Asn Thr Ala Thr Cys Ala Thr Gln Arg Leu Ala Asn Phe Leu Val
1               5                   10                  15

His Ser Ser Asn Asn Phe Gly Ala Ile Leu Ser Ser Thr Asn Val Gly
                20                  25                  30

Ser Asn Thr Tyr
            35

(2) INFORMATION FOR SEQ ID NO: 8:

(i) SEQUENCE CHARACTERISTICS:
            (A) LENGTH: 37 amino acids
            (B) TYPE: amino acid
            (C) STRANDEDNESS: single
```

```
        (D) TOPOLOGY: linear (ii) MOLECULE TYPE: peptide (ix) FEATURE:
        (B) LOCATION: 37
        (D) OTHER INFORMATION: amidated Tyr (Tyrosinamide)

(xi) SEQUENCE DESCRIPTION: SEQ ID NO: 8:

Lys Cys Asn Thr Ala Thr Cys Ala Thr Gln Arg Leu Ala Asn Phe Leu
1               5                  10                  15

Val His Ser Ser Asn Asn Phe Gly Ala Ile Leu Pro Ser Thr Asn Val
            20                  25                  30

Gly Ser Asn Thr Tyr
        35

(2) INFORMATION FOR SEQ ID NO: 9:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (ix) FEATURE:
        (B) LOCATION: 37
        (D) OTHER INFORMATION: amidated Tyr (Tyrosinamide)

(xi) SEQUENCE DESCRIPTION: SEQ ID NO: 9:

Lys Cys Asn Thr Ala Thr Cys Ala Thr Gln Arg Leu Ala Asn Phe Leu
1               5                  10                  15

Val His Ser Ser Asn Asn Phe Gly Pro Ile Leu Pro Pro Thr Asn Val
            20                  25                  30

Gly Ser Asn Thr Tyr
        35

(2) INFORMATION FOR SEQ ID NO: 10:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (ix) FEATURE:
        (B) LOCATION: 37
        (D) OTHER INFORMATION: amidated Tyr (Tyrosinamide)

(xi) SEQUENCE DESCRIPTION: SEQ ID NO: 10:

Lys Cys Asn Thr Ala Thr Cys Ala Thr Gln Arg Leu Ala Asn Phe Leu
1               5                  10                  15

Val Arg Ser Ser Asn Asn Phe Gly Pro Ile Leu Pro Ser Thr Asn Val
            20                  25                  30

Gly Ser Asn Thr Tyr
        35

(2) INFORMATION FOR SEQ ID NO: 11:

(i) SEQUENCE CHARACTERISTICS:
        (A) LENGTH: 36 amino acids
        (B) TYPE: amino acid
        (C) STRANDEDNESS: single
        (D) TOPOLOGY: linear
```

```
    (ii) MOLECULE TYPE: peptide (ix) FEATURE:
         (B) LOCATION: 36
         (D) OTHER INFORMATION: amidated Tyr (Tyrosinamide)

(xi) SEQUENCE DESCRIPTION: SEQ ID NO: 11:

Cys Asn Thr Ala Thr Cys Ala Thr Gln Arg Leu Ala Asn Phe Leu Val
1               5                   10                  15

His Arg Ser Asn Asn Phe Gly Pro Ile Leu Pro Ser Thr Asn Val
            20                  25                  30

Gly Ser Asn Thr Tyr
            35

(2) INFORMATION FOR SEQ ID NO: 12:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (ix) FEATURE:
         (B) LOCATION: 37
         (D) OTHER INFORMATION: amidated Tyr (Tyrosinamide)

(xi) SEQUENCE DESCRIPTION: SEQ ID NO: 12:

Lys Cys Asn Thr Ala Thr Cys Ala Thr Gln Arg Leu Ala Asn Phe Leu
1               5                   10                  15

Val His Ser Ser Asn Asn Phe Gly Pro Val Leu Pro Pro Thr Asn Val
            20                  25                  30

Gly Ser Asn Thr Tyr
        35

(2) INFORMATION FOR SEQ ID NO: 13:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (ix) FEATURE:
         (B) LOCATION: 37
         (D) OTHER INFORMATION: amidated Tyr (Tyrosinamide)

(xi) SEQUENCE DESCRIPTION: SEQ ID NO: 13:

Lys Cys Asn Thr Ala Thr Cys Ala Thr Gln Arg Leu Ala Asn Phe Leu
1               5                   10                  15

Val Arg Ser Ser Asn Asn Phe Gly Pro Ile Leu Pro Pro Thr Asn Val
            20                  25                  30

Gly Ser Asn Thr Tyr
        35

(2) INFORMATION FOR SEQ ID NO: 14:

(i) SEQUENCE CHARACTERISTICS:
        (A) LENGTH: 36 amino acids
        (B) TYPE: amino acid
        (C) STRANDEDNESS: single
        (D) TOPOLOGY: linear
```

(ii) MOLECULE TYPE: peptide (ix) FEATURE:
            (B) LOCATION: 36
            (D) OTHER INFORMATION: amidated Tyr (Tyrosinamide)

(xi) SEQUENCE DESCRIPTION: SEQ ID NO: 14:

Cys Asn Thr Ala Thr Cys Ala Thr Gln Arg Leu Ala Asn Phe Leu Val
1               5                   10                  15

Arg Ser Ser Asn Asn Phe Gly Pro Ile Leu Pro Pro Ser Asn Val Gly
            20                  25                  30

Ser Asn Thr Tyr
        35

(2) INFORMATION FOR SEQ ID NO: 15:

(i) SEQUENCE CHARACTERISTICS:
            (A) LENGTH: 36 amino acids
            (B) TYPE: amino acid
            (C) STRANDEDNESS: single
            (D) TOPOLOGY: linear (ii) MOLECULE TYPE: protein (ix) FEATURE:
            (B) LOCATION: 36
            (D) OTHER INFORMATION: amidated Tyr (Tyrosinamide)

(xi) SEQUENCE DESCRIPTION: SEQ ID NO: 15:

Cys Asn Thr Ala Thr Cys Ala Thr Gln Arg Leu Ala Asn Phe Leu Val
1               5                   10                  15

His Ser Ser Asn Asn Phe Gly Pro Ile Leu Pro Pro Ser Asn Val Gly
            20                  25                  30

Ser Asn Thr Tyr
        35

(2) INFORMATION FOR SEQ ID NO: 16:

(i) SEQUENCE CHARACTERISTICS:
            (A) LENGTH: 37 amino acids
            (B) TYPE: amino acid
            (C) STRANDEDNESS: single
            (D) TOPOLOGY: linear (ii) MOLECULE TYPE: protein (ix) FEATURE:
            (B) LOCATION: 37
            (D) OTHER INFORMATION: amidated Tyr (Tyrosinamide)

(xi) SEQUENCE DESCRIPTION: SEQ ID NO: 16:

Lys Cys Asn Thr Ala Thr Cys Ala Thr Gln Arg Leu Ala Asn Phe Leu
1               5                   10                  15

Val His Ser Ser Asn Asn Leu Gly Pro Val Leu Pro Pro Thr Asn Val
            20                  25                  30

Gly Ser Asn Thr Tyr
        35

(2) INFORMATION FOR SEQ ID NO: 17:

(i) SEQUENCE CHARACTERISTICS:
            (A) LENGTH: 37 amino acids
            (B) TYPE: amino acid
            (C) STRANDEDNESS: single
            (D) TOPOLOGY: linear (ii) MOLECULE TYPE: protein (ix) FEATURE:
            (B) LOCATION: 37
            (D) OTHER INFORMATION: amidated Tyr (Tyrosinamide)

(xi) SEQUENCE DESCRIPTION: SEQ ID NO: 17:

Lys Cys Asn Thr Ala Thr Cys Ala Thr Gln Arg Leu Ala Asn Phe Leu
1               5                   10                  15

Val His Ser Ser Asn Asn Leu Gly Pro Val Leu Pro Ser Thr Asn Val
            20                  25                  30

Gly Ser Asn Thr Tyr
        35

(2) INFORMATION FOR SEQ ID NO: 18:

(i) SEQUENCE CHARACTERISTICS:
            (A) LENGTH: 36 amino acids
            (B) TYPE: amino acid
            (C) STRANDEDNESS: single
            (D) TOPOLOGY: linear (ii) MOLECULE TYPE: protein (ix) FEATURE:
            (B) LOCATION: 36
            (D) OTHER INFORMATION: amidated Tyr (Tyrosinamide)

(xi) SEQUENCE DESCRIPTION: SEQ ID NO: 18:

Cys Asn Thr Ala Thr Cys Ala Thr Gln Arg Leu Ala Asn Phe Leu Val
1               5                   10                  15

His Ser Ser Asn Asn Leu Gly Pro Val Leu Pro Ser Thr Asn Val Gly
            20                  25                  30

Ser Asn Thr Tyr
        35

(2) INFORMATION FOR SEQ ID NO: 19:

(i) SEQUENCE CHARACTERISTICS:
            (A) LENGTH: 37 amino acids
            (B) TYPE: amino acid
            (C) STRANDEDNESS: single
            (D) TOPOLOGY: linear (ii) MOLECULE TYPE: protein (ix) FEATURE:
            (B) LOCATION: 37
            (D) OTHER INFORMATION: amidated Tyr (Tyrosinamide)

(xi) SEQUENCE DESCRIPTION: SEQ ID NO: 19:

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Ser Thr Asn Val
            20                  25                  30

Gly Ser Asn Thr Tyr
        35

(2) INFORMATION FOR SEQ ID NO: 20:

(i) SEQUENCE CHARACTERISTICS:
            (A) LENGTH: 37 amino acids
            (B) TYPE: amino acid
            (C) STRANDEDNESS: single
            (D) TOPOLOGY: linear (ii) MOLECULE TYPE: protein (ix) FEATURE:
           (B) LOCATION: 37
           (D) OTHER INFORMATION: amidated Tyr (Tyrosinamide)

(xi) SEQUENCE DESCRIPTION: SEQ ID NO: 20:

Lys Cys Asn Thr Ala Thr Cys Ala Thr Gln Arg Leu Ala Asn Phe Leu
1               5                   10                  15

Val Arg Ser Ser Asn Asn Leu Gly Pro Ile Leu Pro Pro Thr Asn Val
            20                  25                  30

Gly Ser Asn Thr Tyr
        35

(2) INFORMATION FOR SEQ ID NO: 21:

(i) SEQUENCE CHARACTERISTICS:
           (A) LENGTH: 37 amino acids
           (B) TYPE: amino acid
           (C) STRANDEDNESS: single
           (D) TOPOLOGY: linear (ii) MOLECULE TYPE: protein (ix) FEATURE:
           (B) LOCATION: 37
           (D) OTHER INFORMATION: amidated Tyr (Tyrosinamide)

(xi) SEQUENCE DESCRIPTION: SEQ ID NO: 21:

Lys Cys Asn Thr Ala Thr Cys Ala Thr Gln Arg Leu Ala Asn Phe Leu
1               5                   10                  15

Val Arg Ser Ser Asn Asn Leu Gly Pro Ile Leu Pro Ser Thr Asn Val
            20                  25                  30

Gly Ser Asn Thr Tyr
        35

(2) INFORMATION FOR SEQ ID NO: 22:

(i) SEQUENCE CHARACTERISTICS:
           (A) LENGTH: 37 amino acids
           (B) TYPE: amino acid
           (C) STRANDEDNESS: single
           (D) TOPOLOGY: linear (ii) MOLECULE TYPE: protein (ix) FEATURE:
           (B) LOCATION: 37
           (D) OTHER INFORMATION: amidated Tyr (Tyrosinamide)

(xi) SEQUENCE DESCRIPTION: SEQ ID NO: 22:

Lys Cys Asn Thr Ala Thr Cys Ala Thr Gln Arg Leu Ala Asn Phe Leu
1               5                   10                  15

Ile His Ser Ser Asn Asn Leu Gly Pro Ile Leu Pro Pro Thr Asn Val
            20                  25                  30

Gly Ser Asn Thr Tyr
        35

(2) INFORMATION FOR SEQ ID NO: 23:

(i) SEQUENCE CHARACTERISTICS:
           (A) LENGTH: 37 amino acids
           (B) TYPE: amino acid
           (C) STRANDEDNESS: single
           (D) TOPOLOGY: linear (ii) MOLECULE TYPE: protein (ix) FEATURE:

(B) LOCATION: 37
            (D) OTHER INFORMATION: amidated Tyr (Tyrosinamide)

(xi) SEQUENCE DESCRIPTION: SEQ ID NO: 23:

Lys Cys Asn Thr Ala Thr Cys Ala Thr Gln Arg Leu Ala Asn Phe Leu
1               5                   10                  15

Val Ile Ser Ser Asn Asn Phe Gly Pro Ile Leu Pro Pro Thr Asn Val
            20                  25                  30

Gly Ser Asn Thr Tyr
        35

(2) INFORMATION FOR SEQ ID NO: 24:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: protein (ix) FEATURE:
        (B) LOCATION: 36
        (D) OTHER INFORMATION: amidated Tyr (Tyrosinamide)

(xi) SEQUENCE DESCRIPTION: SEQ ID NO: 24:

Cys Asn Thr Ala Thr Cys Ala Thr Gln Arg Leu Ala Asn Phe Leu Ile
1               5                   10                  15

His Ser Ser Asn Asn Leu Gly Pro Ile Leu Pro Pro Thr Asn Val Gly
            20                  25                  30

Ser Asn Thr Tyr
        35

(2) INFORMATION FOR SEQ ID NO: 25:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: protein (ix) FEATURE:
        (B) LOCATION: 37
        (D) OTHER INFORMATION: amidated Tyr (Tyrosinamide)

(xi) SEQUENCE DESCRIPTION: SEQ ID NO: 25:

Lys Cys Asn Thr Ala Thr Cys Ala Thr Gln Arg Leu Ala Asn Phe Leu
1               5                   10                  15

Ile Arg Ser Ser Asn Asn Leu Gly Ala Ile Leu Ser Ser Thr Asn Val
            20                  25                  30

Gly Ser Asn Thr Tyr
        35

(2) INFORMATION FOR SEQ ID NO: 26:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: protein (ix) FEATURE:
        (B) LOCATION: 37

(D) OTHER INFORMATION: amidated Tyr (Tyrosinamide)

(xi) SEQUENCE DESCRIPTION: SEQ ID NO: 26:

Lys Cys Asn Thr Ala Thr Cys Ala Thr Gln Arg Leu Ala Asn Phe Leu
1               5                   10                  15

Ile Arg Ser Ser Asn Asn Leu Gly Ala Val Leu Ser Pro Thr Asn Val
            20                  25                  30

Gly Ser Asn Thr Tyr
        35

(2) INFORMATION FOR SEQ ID NO: 27:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: protein (ix) FEATURE:
        (B) LOCATION: 37
        (D) OTHER INFORMATION: amidated Tyr (Tyrosinamide)

(xi) SEQUENCE DESCRIPTION: SEQ ID NO: 27:

Lys Cys Asn Thr Ala Thr Cys Ala Thr Gln Arg Leu Ala Asn Phe Leu
1               5                   10                  15

Ile Arg Ser Ser Asn Asn Leu Gly Pro Val Leu Pro Pro Thr Asn Val
            20                  25                  30

Gly Ser Asn Thr Tyr
        35

(2) INFORMATION FOR SEQ ID NO: 28:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: protein (ix) FEATURE:
        (B) LOCATION: 37
        (D) OTHER INFORMATION: amidated Tyr (Tyrosinamide)

(xi) SEQUENCE DESCRIPTION: SEQ ID NO: 28:

Lys Cys Asn Thr Ala Thr Cys Ala Thr Gln Arg Leu Thr Asn Phe Leu
1               5                   10                  15

Val His Ser Ser His Asn Leu Gly Ala Ala Leu Leu Pro Thr Asp Val
            20                  25                  30

Gly Ser Asn Thr Tyr
        35

(2) INFORMATION FOR SEQ ID NO: 29:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: protein (ix) FEATURE:
        (B) LOCATION: 37
        (D) OTHER INFORMATION: amidated Tyr (Tyrosinamide)

(xi) SEQUENCE DESCRIPTION: SEQ ID NO: 29:

Lys Cys Asn Thr Ala Thr Cys Ala Thr Gln Arg Leu Thr Asn Phe Leu
1               5                   10                  15

Val His Ser Ser His Asn Leu Gly Ala Ala Leu Ser Pro Thr Asp Val
            20                  25                  30

Gly Ser Asn Thr Tyr
        35

(2) INFORMATION FOR SEQ ID NO: 30:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: protein (ix) FEATURE:
        (B) LOCATION: 36
        (D) OTHER INFORMATION: amidated Tyr (Tyrosinamide)

(xi) SEQUENCE DESCRIPTION: SEQ ID NO: 30:

Cys Asn Thr Ala Thr Cys Ala Thr Gln Arg Leu Thr Asn Phe Leu Val
1               5                   10                  15

His Ser Ser His Asn Leu Gly Ala Val Leu Pro Ser Thr Asp Val Gly
            20                  25                  30

Ser Asn Thr Tyr
        35

(2) INFORMATION FOR SEQ ID NO: 31:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: protein (ix) FEATURE:
        (B) LOCATION: 37
        (D) OTHER INFORMATION: amidated Tyr (Tyrosinamide)

(xi) SEQUENCE DESCRIPTION: SEQ ID NO: 31:

Lys Cys Asn Thr Ala Thr Cys Ala Thr Gln Arg Leu Thr Asn Phe Leu
1               5                   10                  15

Val Arg Ser Ser His Asn Leu Gly Ala Ala Leu Ser Pro Thr Asp Val
            20                  25                  30

Gly Ser Asn Thr Tyr
        35

(2) INFORMATION FOR SEQ ID NO: 32:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: protein (ix) FEATURE:
        (B) LOCATION: 37
        (D) OTHER INFORMATION: amidated Tyr (Tyrosinamide)

(xi) SEQUENCE DESCRIPTION: SEQ ID NO: 32:

Lys Cys Asn Thr Ala Thr Cys Ala Thr Gln Arg Leu Thr Asn Phe Leu
1               5                   10                  15

Val Arg Ser Ser His Asn Leu Gly Ala Ile Leu Pro Pro Thr Asp Val
                20                  25                  30

Gly Ser Asn Thr Tyr
            35

(2) INFORMATION FOR SEQ ID NO: 33

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: protein (ix) FEATURE:
        (B) LOCATION: 37
        (D) OTHER INFORMATION: amidated Tyr (Tyrosinamide)

(xi) SEQUENCE DESCRIPTION: SEQ ID NO: 33:

Lys Cys Asn Thr Ala Thr Cys Ala Thr Gln Arg Leu Thr Asn Phe Leu
1               5                   10                  15

Val Arg Ser Ser His Asn Leu Gly Pro Ala Leu Pro Pro Thr Asp Val
                20                  25                  30

Gly Ser Asn Thr Tyr
            35

(2) INFORMATION FOR SEQ ID NO: 34

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: protein (ix) FEATURE:
        (B) LOCATION: 37
        (D) OTHER INFORMATION: amidated Tyr (Tyrosinamide)

(xi) SEQUENCE DESCRIPTION: SEQ ID NO: 34:

Lys Asp Asn Thr Ala Thr Lys Ala Thr Gln Arg Leu Ala Asn Phe Leu
1               5                   10                  15

Val His Ser Ser Asn Asn Phe Gly Ala Ile Leu Ser Ser Thr Asn Val
                20                  25                  30

Gly Ser Asn Thr Tyr
            35

(2) INFORMATION FOR SEQ ID NO: 35

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: protein (ix) FEATURE:
        (B) LOCATION: 37
        (D) OTHER INFORMATION: amidated Tyr (Tyrosinamide)

(xi) SEQUENCE DESCRIPTION: SEQ ID NO: 35:

```
Ala Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

(2) INFORMATION FOR SEQ ID NO: 36

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: protein (ix) FEATURE:
        (B) LOCATION: 37
        (D) OTHER INFORMATION: amidated Tyr (Tyrosinamide)

(xi) SEQUENCE DESCRIPTION: SEQ ID NO: 36:

Ser Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

(2) INFORMATION FOR SEQ ID NO: 37

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: protein (ix) FEATURE:
        (B) LOCATION: 37
        (D) OTHER INFORMATION: amidated Tyr (Tyrosinamide)

(xi) SEQUENCE DESCRIPTION: SEQ ID NO: 37:

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Pro Thr Asn Val
            20                  25                  30

Gly Ser Asn Thr Tyr
        35

(2) INFORMATION FOR SEQ ID NO: 38

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: protein (ix) FEATURE:
        (B) LOCATION: 37
        (D) OTHER INFORMATION: amidated Tyr (Tyrosinamide)

(xi) SEQUENCE DESCRIPTION: SEQ ID NO: 38:
```

```
Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Ser Thr Asn Val
                20                  25                  30

Gly Ser Asn Thr Tyr
            35

(2) INFORMATION FOR SEQ ID NO: 39

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: protein (ix) FEATURE:
        (B) LOCATION: 36
        (D) OTHER INFORMATION: amidated Tyr (Tyrosinamide)

(xi) SEQUENCE DESCRIPTION: SEQ ID NO: 39:

Cys Asn Thr Ala Thr Cys Ala Thr Gln Arg Leu Ala Asn Phe Leu Val
1               5                   10                  15

His Ser Ser Asn Asn Phe Gly Pro Ile Leu Pro Ser Thr Asn Val Gly
                20                  25                  30

Ser Asn Thr Tyr
            35

(2) INFORMATION FOR SEQ ID NO: 40

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: protein (ix) FEATURE:
        (B) LOCATION: 36
        (D) OTHER INFORMATION: amidated Tyr (Tyrosinamide)

(xi) SEQUENCE DESCRIPTION: SEQ ID NO: 40:

Cys Asn Thr Ala Thr Cys Ala Thr Gln Arg Leu Ala Asn Phe Leu Val
1               5                   10                  15

His Ser Ser Asn Asn Phe Gly Pro Val Leu Pro Pro Ser Asn Val Gly
                20                  25                  30

Ser Asn Thr Tyr
            35

(2) INFORMATION FOR SEQ ID NO: 41

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: protein (ix) FEATURE:
        (B) LOCATION: 11
        (D) OTHER INFORMATION: Arg is a D amino acid residue (xi) SEQUENCE DESCRIPTION: SEQ ID NO: 41:

Lys Cys Asn Thr Ala Thr Cys Ala Thr Gln Arg Leu Ala Asn Phe Leu
```

-continued

```
         1               5              10              15
Val His Ser Ser Asn Asn Phe Gly Ala Ile Leu Ser Ser Thr Asn Val
                20              25              30
Gly Ser Asn Thr Tyr
         35
```